(12) United States Patent
Perambakam et al.

(10) Patent No.: US 8,557,777 B2
(45) Date of Patent: Oct. 15, 2013

(54) METHODS FOR TREATING CANCER USING PROSTATE SPECIFIC ANTIGEN AND TUMOR ENDOTHELIAL MARKER PEPTIDES

(75) Inventors: Supriya M. Perambakam, Oak Park, IL (US); David J. Peace, Chicago, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 0 days.

(21) Appl. No.: 13/413,242

(22) Filed: Mar. 6, 2012

(65) Prior Publication Data
US 2012/0230939 A1 Sep. 13, 2012

Related U.S. Application Data

(63) Continuation-in-part of application No. PCT/US2011/043598, filed on Jul. 11, 2011.

(60) Provisional application No. 61/426,321, filed on Dec. 22, 2010, provisional application No. 61/363,091, filed on Jul. 9, 2010, provisional application No. 61/449,884, filed on Mar. 7, 2011.

(51) Int. Cl.
| A61K 38/04 | (2006.01) |
| A61K 38/08 | (2006.01) |
| A61K 38/10 | (2006.01) |
| A61K 38/17 | (2006.01) |
| C07K 7/06 | (2006.01) |
| C07K 7/08 | (2006.01) |
| C07K 14/705 | (2006.01) |

(52) U.S. Cl.
USPC ....... 514/19.2; 514/19.5; 514/21.4; 514/21.6; 530/326; 530/328

(58) Field of Classification Search
None
See application file for complete search history.

(56) References Cited

U.S. PATENT DOCUMENTS

| 5,478,556 A * | 12/1995 | Elliott et al. ............. 424/85.2 |
| 5,807,978 A | 9/1998 | Kokolus et al. |
| 6,689,355 B2 | 2/2004 | Schultes et al. |
| 7,288,636 B2 | 10/2007 | Mikolajczyk et al. |
| 7,531,629 B2 * | 5/2009 | Eisenbach et al. ........... 530/350 |
| 2008/0095790 A1 | 4/2008 | Perambakam et al. |

FOREIGN PATENT DOCUMENTS

| CA | 2319252 A1 | 7/1999 |
| CA | 2389176 A1 | 5/2001 |
| CA | 2468258 A1 | 6/2003 |
| CA | 2731823 A1 | 1/2010 |
| CA | 2748823 A1 | 7/2010 |
| WO | WO 2007/063421 A2 * | 6/2007 |
| WO | WO-2008/000734 A1 | 1/2008 |
| WO | WO-2008/126413 A1 | 10/2008 |
| WO | WO 2008/126413 A1 * | 10/2008 |

OTHER PUBLICATIONS

Banchereau et al., Immune and clinical responses in patients with metastatic melanoma to CD34(+) progenitor-derived dendritic cell vaccine, Cancer Res., 61(17):6451-8 (2001).

Carbone et al., Immunization with mutant p53- and K-ras-derived peptides in cancer patients: immune response and clinical outcome, J. Clin. Oncol., 23(22):5099-107 (2005).

Chang et al., Prostate-specific membrane antigen is produced in tumor-associated neovasculature, Clin. Cancer Res., 5(10):2674-81 (1999).

Chen et al., Selection of anthrax toxin protective antigen variants that discriminate between the cellular receptors TEM8 and CMG2 and achieve targeting of tumor cells, J. Biol. Chem., 282(13):9834-45 (2007).

Davies et al., Elevated levels of tumour endothelial marker-8 in human breast cancer and its clinical significance, Int. J. Oncol., 29(5):1311-7 (2006).

Disis et al., Generation of T-cell immunity to the HER-2/neu protein after active immunization with HER-2/neu peptide-based vaccines, J. Clin. Oncol., 20(11):2624-32 (2002).

Disis et al., Granulocyte-macrophage colony-stimulating factor: an effective adjuvant for protein and peptide-based vaccines, Blood, 88(1):202-10 (1996).

Falk et al., Allele-specific motifs revealed by sequencing of self-peptides eluted from MHC molecules, Nature, 351(6324):290-6 (1991).

Flower, Towards in silico prediction of immunogenic epitopes, Trends in Immunol., 24(12):667-74 (2003).

Folkman et al., Angiogenesis, J. Biol. Chem., 267(16):10931-4 (1992).

Ford et al., Immunocytochemical localisation of prostate-specific antigen: specificity and application to clinical practice, Br. J. Urol., 57(1):50-5 (1985).

Genbank Accession No. P07288, (created: Apr. 1, 1988, updated: Jul. 1, 1989).

Gulley et al., Immunologic and prognostic factors associated with overall survival employing a poxviral-based PSA vaccine in metastatic castrate-resistant prostate cancer, Cancer Immunol. Immunother., 59(5):663-74 (2010).

Haralambieva et al., 2'-5'-Oligoadenylate synthetase single-nucleotide polymorphisms and haplotypes are associated with variations in immune responses to rubella vaccine, Hum. Immunol., 71(4):383-91 (2010).

Hofmeister et al., Tumor stroma-associated antigens for anti-cancer immunotherapy, Cancer Immunol. Immunother., 55(5):481-94 (2006).

Hotchkiss et al., TEM8 expression stimulates endothelial cell adhesion and migration by regulating cell-matrix interactions on collagen, Exp. Cell Res., 305(1):133-44 (2005).

(Continued)

*Primary Examiner* — Xiaozhen Xie

(74) *Attorney, Agent, or Firm* — Marshall, Gerstein & Borun LLP

(57) ABSTRACT

The present invention is directed to prostate specific antigen (PSA) and tumor endothelial marker 8 (TEM8) peptide compositions and methods for treating cancer with the compositions.

18 Claims, 12 Drawing Sheets

(56) References Cited

OTHER PUBLICATIONS

Irizarry et al., Summary of Affymetrix GeneChip probe level data, Nucleic Acids Res., 31(4):e15 (2003).
Ishikazi et al., Inhibition of tumor growth with antiangiogenic cancer vaccine using epitope peptides derived from human vascular endothelial growth factor receptor 1, Clin. Cancer Res., 12(19):5841-9 (2006).
Jemal et al., Cancer statistics, 2009, CA Cancer J. Clin., 59(4):225-49 (2009).
Kammertoens et al., Immunotherapy: target the stroma to hit the tumor, Trends Mol. Med., 11(5):225-31 (2005).
Kantoff et al., Updated survival results of the IMPACT trial of sipuleucel-T for metastatic castration-resistant prostate cancer (CRPC), Abstract 8, 2010 Genitourinary Cancers Symposium, American Society of Clinical Oncology (2010).
Khan et al., EDB fibronectin and angiogenesis—a novel mechanistic pathway, Angiogenesis, 8(3):183-96 (2005).
Kim et al., Direct detection and magnetic isolation of *Chlamydia trachomatis* major outer membrane protein-specific CD8+ CTLs with HLA class I tetramers, J. Immunol., 165:7285-92 (2000).
Lau et al., Phase I trial of intravenous peptide-pulsed dendritic cells in patients with metastatic melanoma, J. Immunother., 24(1):66-78 (2001).
Li et al., CD8Tc1 and Tc2 cells secrete distinct cytokine patterns in vitro and in vivo but induce similar inflammatory reactions, J. Immunol., 158(9):4152-61 (1997).
Maia et al., Characterization of oligoadenylate synthetase-1 expression in rat mammary gland and prostate: effects of 17beta-estradiol on the regulation of OAS1g in both tissues, Mol. Cell Biochem., 314(1-2):113-21 (2008).
Markovic et al., Peptide vaccination of patients with metastatic melanoma: improved clinical outcome in patients demonstrating effective immunization, Am. J. Clin. Oncol., 29(4):352-60 (2006).
Meidenbauer et al., Generation of PSA-reactive effector cells after vaccination with a PSA-based vaccine in patients with prostate cancer, Prostate, 43(2):88-100 (2000).
Mittendorf et al., Evaluation of the HER2/neu-derived peptide GP2 for use in a peptide-based breast cancer vaccine trial, Cancer, 106(11):2309-17 (2006).
Nestle et al., Vaccination of melanoma patients with peptide- or tumor lysate-pulsed dendritic cells, Nat. Med., 4(3):328-32 (1998).
Palucka et al., Taming cancer by inducing immunity via dendritic cells, Immunol. Rev., 220:129-50 (2007).
Parker et al., Scheme for ranking potential HLA-A2 binding peptides based on independent binding of individual peptide side-chains, J. Immunol., 152(1):163-75 (1994).
Peoples et al., Clinical trial results of a HER2/neu (E75) vaccine to prevent recurrence in high-risk breast cancer patients, J. Clin. Oncol., 23(30):7536-45 (2005).
Perambakam et al., Induction of specific T cell immunity in patients with prostate cancer by vaccination with PSA146-154 peptide, Cancer Immunol. Immunother., 55(9):1033-42 (2006).
Perambakam et al., Induction of Tc2 cells with specificity for prostate-specific antigen from patients with hormone-refractory prostate cancer, Cancer Immunol. Immunother., 51 (5):263-70 (2002).
Perambakam et al., Long-term follow-up of HLA-A2+ patients with high-risk, hormone-sensitive prostate cancer vaccinated with the prostate specific antigen peptide homologue (PSA146-154), Clin Dev. Immunol., 2010:473-53 (2010).
Pronzato et al., Hormonotherapy of advanced prostate cancer, Ann. Oncol., 16 (Suppl. 4):iv80-iv84 (2005).
Qin et al., A critical requirement of interferon gamma-mediated angiostasis for tumor rejection by CD8+ T cells, Cancer Res., 63(14):4095-100 (2003).
Qin et al., CD4+ T cell—mediated tumor rejection involves inhibition of angiogenesis that is dependent on IFN gamma receptor expression by nonhematopoietic cells, Immunity, 12(6):677-86 (2000).
Rammensee et al., SYFPEITHI: database for MHC ligands and peptide motifs, Immunogenetics, 50(3-4):213-9 (1999).
Remington's Pharmaceutical Sciences, 19th ed., Mack Printing Company, pp. 1289-329 (1990).
Riboldi et al., Cutting edge: proangiogenic properties of alternatively activated dendritic cells, J. Immunol., 175(5):2788-92 (2005).
Rmali et al., Prognostic values of tumor endothelial markers in patients with colorectal cancer, World J. Gastroenterol., 11(9):1283-6 (2005).
Ruan et al., DNA vaccine against tumor endothelial marker 8 inhibits tumor angiogenesis and growth, J. Immunother., 32(5):486-91 (2009).
Saaristo et al., Mechanisms of angiogenesis and their use in the inhibition of tumor growth and metastasis, Oncogene, 19:6122-9 (2000).
Sakai et al., Bcl-2 mediated modulation of vascularization in prostate cancer xenografts, Prostate, 69(5):459-70 (2009).
Singh et al., Genome-wide expression profiing reveals transcriptomic variation and perturbed gene networks in androgen-dependent and androgen-independent prostate, Cancer Lett., 259:28-38 (2008).
St. Croix et al., Genes expressed in human tumor endothelium, Science, 289:1197-1202 (2000).
Thomas-Kaskel et al., Vaccination of advanced prostate cancer patients with PSCA and PSA peptide-loaded dendritic cells induces DTH responses that corelated with superior overall survival, Int. J. Cancer, 119:2428-34 (2006).
Thurner et al., Vaccination with mage-3A1 peptide-pulsed mature, monocyte-derived dendritic cells expands specific cytotoxic T cells and induces regression of some metastases in advanced stage IV melanoma, J. Exp. Med., 190(11):1669-78 (1999).
Timmerman et al., Idiotype-pulsed dendritic cell vaccination for B-cell lymphoma: clinical and immune responses in 35 patients, Blood, 99(5):1517-26 (2002).
Townsend et al., Antigen recognition by class I-restricted T lymphocytes, Ann. Rev. Immunol., 7:601-24 (1989).
Tsai et al., Gene expression profiling of breast, prostate, and glioma cells following single versus fractionated doses of radiation, Cancer Res., 67(8):3845-52 (2007).
Xue et al., Induction of human cytotoxic T lymphocytes specific for prostate-specific antigen, Prostate, 30(2):73-8 (1997).

\* cited by examiner

SEQUENCE LISTING

<160> NUMBER OF SEQ ID NOS: 23

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

Val Ile Ser Asn Asp Val Cys Ala Gln Val His Pro Gln Lys Val Thr
1               5                   10                  15

Lys Phe Met Leu
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide

<400> SEQUENCE: 2

Cys Ala Leu Pro Glu Arg Pro Ser Leu Tyr Thr Lys Val Val His Tyr
1               5                   10                  15

Arg Lys Trp Ile Lys
            20

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Lys Leu Gln Cys Val Asp Leu His Val
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

His Pro Gln Lys Val Thr Lys Phe Met
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

His Pro Gln Lys Val Thr Lys Phe Met Leu
1               5                   10

<210> SEQ ID NO 6
<211> LENGTH: 10
<212> TYPE: PRT
<213> ORGANISM: Artificial Sequence

```
<220> FEATURE:
<223> OTHER INFORMATION: Synthetic peptide

<400> SEQUENCE: 6

His Pro Gln Lys Val Thr Lys Phe Met Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

Ala Leu Pro Glu Arg Pro Ser Leu Tyr Thr
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Ala Leu Pro Glu Arg Pro Ser Leu Tyr
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Val Val His Tyr Arg Lys Trp Ile Lys
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Lys Val Val His Tyr Arg Lys Trp Ile Lys
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Val Val His Tyr Arg Lys Trp Ile Lys
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 12

Lys Val Val His Tyr Arg Lys Trp Ile Lys
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Val Val His Tyr Arg Lys Trp Ile Lys
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Lys Val Val His Tyr Arg Lys Trp Ile Lys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Pro Glu Arg Pro Ser Leu Tyr Thr Lys Val
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Ala Leu Gln Gly Ile Ile His Ser Ile
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Thr Leu Asn Glu Lys Pro Phe Ser Val
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18
```

```
Ser Met Asn Asp Gly Leu Ser Phe Ile
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Phe Leu Leu Leu Ala Leu Ala Leu Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Ala Leu Leu Trp Trp Phe Trp Pro Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Leu Leu Trp Trp Glu Trp Pro Leu Cys
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

Gly Leu Met Trp Trp Phe Trp Pro Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Leu Met Trp Trp Phe Trp Pro Leu Cys
1               5
```

METHODS FOR TREATING CANCER USING PROSTATE SPECIFIC ANTIGEN AND TUMOR ENDOTHELIAL MARKER PEPTIDES

CROSS REFERENCE TO RELATED APPLICATIONS

This application is a continuation-in-part of International Patent Application No. PCT/US2011/043598, filed Jul. 11, 2011, which claims the priority benefit of U.S. Provisional Patent Application Ser. No. 61/363,091, filed Jul. 9, 2010, and U.S. Provisional Patent Application Ser. No. 61/426,321, filed Dec. 22, 2010; the disclosures of which are incorporated herein in their entirety. This application also claims the priority benefit of U.S. Provisional Patent Application Ser. No. 61/449,884, filed Mar. 7, 2011, the disclosure of which is incorporated herein in its entirety.

STATEMENT OF GOVERNMENT INTEREST

This invention was made with government support under grant numbers DAMD17-98-1-8489 awarded by U.S. Army Medical Research and Material Command, and CA088062 awarded by the National Institutes of Health (NIH). The government has certain rights in the invention.

FIELD OF THE INVENTION

The present invention is directed to PSA and TEM8 peptide compositions and methods for treating cancer with the compositions.

BACKGROUND OF THE INVENTION

Prostate cancer (CaP) is the second leading cause of cancer-related mortality in the United States. There were approximately 27,360 deaths caused by CaP in 2009 [Jemal et al., CA: A Cancer Journal for Clinicians, 59(4): 225-249 (2009)]. Patients who recur after primary ablative therapy respond transiently to androgen deprivation therapy but subsequently progress to hormone-refractory disease for which curative systemic therapies are lacking [Pronzato et al., Annals of Oncology, 16 (Suppl. 4) iv: 80-84 (2005)]. Recent studies have demonstrated that overall survival (OS) of patients with hormone refractory CaP can be modestly extended by vaccination with autologous dendritic cells (DC) loaded with recombinant proteins consisting of granulocyte macrophage colony stimulating factor and prostatic acid phosphatase [Kantoff et al., Genitourinary Cancers Symposium, American Society of Clinical Oncology, Abstract #8 (2010)]. It is widely assumed that improved outcomes might be achieved by vaccinating patients at earlier points in the development of their disease at a time when host immune effector mechanisms remain robust.

The FDA's approval of Sipuleucel-T for the treatment of advanced prostate cancer was a landmark event. The studies leading to the approval of Sipuleucel as well as suggestive results from other prostate cancer vaccine protocols, notably Prostvac® and GVAX, indicates that the clinical course of prostate cancer can be favorably altered by immunotherapeutic manipulation.

Angiogenesis is a complex multistep process involving degradation of the extracellular matrix, endothelial cell (EC) migration, proliferation, and re-differentiation into patent vessels [Folkman and Shing, J Bio Chem. 1992, 267, 10931-10934; Saaristo et al., Oncogene. 2000 Dec. 11; 19 (53): 6122-9]. Angiogenesis is normally observed only transiently under physiological conditions such as embryogenesis, wound healing and reproductive functions in adults. Under pathological conditions such as cancer, abnormal angiogenesis supports the survival and progression of human tumors. Tumor angiogenesis is characterized by abnormal vasculature, and hence the targeted disruption of tumor vasculature is an area of growing interest in cancer biology and therapeutics.

Tumor vasculature express distinct proteins, also called angiogenesis-associated proteins, such as, the prostate-specific membrane antigen, extradomain-B fibronectin, and tumor endothelial marker (TEM) [Chang et al., Clin Cancer Res 1999; 5:2674-2681; Khan et al., Angiogenesis 2005; 8(3):183-96; St Croix et al., Science. 2000 Aug. 18; 289 (5482):1197-202]. TEM8 is a type-I transmembrane cell-surface protein that is found on tumor blood vessels but not normal adult vasculature or somatic tissues [Hotchkiss et al., Exp Cell Res 2005; 305:133-144; Qin et al., Immunity. 2000 June; 12(6):677-86]. International Publication No. WO 2008/00734 published Jan. 3, 2008 and International Publication No. WO 2008/126413 published Oct. 23, 2008 also relate to TEM8. TEM8 was initially identified in St. Croix et al., as a gene that is predominantly expressed in tumor endothelium [Science. 2000, 289(5482):1197-1202]. However, recent evidence indicates that TEM8 also is expressed on certain tumor cells, tumor associated macrophages and some dendritic cells that have been cultured in vitro with specific cytokine cocktails [Hofineister et al., Cancer Immunol Immunother. 2006 May; 55(5):481-94. Epub 2005 Oct. 12; Kammertoens et al., Trends Mol. Med. 2005 May; 11(5):225-31; Riboldi et al., J Immunol 2005, 175:2788-2792]. Interestingly, the TEM8 gene has been shown to encode the anthrax toxin receptor and shares a high degree of amino acid identity with CMG2 protein in the extracellular integrin-like I domain as well as a conserved metal ion dependent adhesion site motif. TEM8 and CMG2 type-I transmembrane proteins belong to a larger family of the von Willebrand factor type-A domain [Chen et al., J Biol. Chem. 2007 Mar. 30; 282(13):9834-45. Epub 2007 Jan 24].

The immunogenic potential of human TEM8 DNA has been recently reported in a B16F10 murine model [Ruan Z et al, J Immunother 2009; 32:486-491], but TEM8 specific CD8+ CTL responses have apparently not been reported in patients with prostate cancer (CaP). The TEM8 gene was stated to be up regulated in an androgen independent human LNCaP variant line [Singh A P et al, Cancer Lett 2008; 259:28-38]. TEM8 protein was reported to be over expressed in PC-3-Bcl-2 positive CaP tissue xenografts along with other key pro-angiogenic and lympho-angiogenic factors [Sakai et al, Prostate 2009; 69:459-470]. TEM8 expression has also been associated with both nodal involvement and disease progression in colon cancer [Rmali et al., World J. Gastroenterol. 2005 Mar. 7; 11(9):1283-6]. Similarly, elevated levels of TEM8 have been correlated with shorter survival in breast cancer patients [Davies et al., Int J. Oncol. 2006 November; 29(5):1311-7].

Various laboratories have utilized peptide-based cancer vaccines that target tumor-associated antigens (TAA) for active immunotherapy of various tumors [Carbone et al., J Clin Oncol 2005 Aug. 1; 23(22):5099-107. Epub 2005 Jun. 27; Markovic et al., Am J Clin Oncol. 2006 August; 29(4): 352-6016; Mittendorf et al., Cancer. 2006 Jun. 1; 106(11): 2309-1717; Perambakam et al., Cancer Immunol Immunother. 2006 September; 55(9):1033-42. Epub 2005 Nov. 10]. Recently, there has been growing interest in the potential of anti-angiogenic T cell-based immunotherapy [Hofineister et al., supra; Ishizaki et al., Clin Cancer Res 2006; 12(19):5841-5849; Kammertoens et al., Trends Mol. Med. 2005 May; 11(5):225-31]. Tumor vasculature or tumor stroma serve as a target for immune intervention as endothelial cells (EC) are genetically stable and are not prone to mutations or loss of MHC antigen expression and therefore, are less likely to demonstrate immune escape, compared to tumor cells [Hofineister et al., Cancer Immunol Immunother. 2006, 55(5):481-494. Epub 2005 Oct. 12]. Further, EC are more accessible to the bloodstream than tumor cells which are often encapsulated or blocked off by anatomical barriers and hence, are more efficiently reached by cytotoxic lymphocytes.

Cytotoxic T lymphocytes (CTL) recognize processed peptide antigens presented in association with class I MHC molecules [Townsend and Bodmer, Ann Rev Immunol 7:601-624, 1989]. The ability of a peptide to elicit specific CTL is contingent on its ability to bind to appropriately restricted class I MHC molecule. Allele-specific peptide sequence motifs have been identified for various class I MHC molecules, including, HLA-0201 allele, the most common class I MHC allele in the U.S. population. Previous work identified a 9-mer HLA-A0201 restricted peptide epitope of prostate-specific antigen that elicited specific CTL responses in vitro from normal individuals and patients with prostate cancer [Perambakam et al., Cancer Immunol Immunother. 2002 July; 51(5):263-70; Xue et al., Prostate 1997; 30:73-78]. See also, U.S. Patent Publication No. 2008/0095790 published Apr. 24, 2008.

There, however, remains a need in the art for additional compositions/vaccines for the treatment of prostate cancer and a need in the art for compositions/vaccines for the treatment other cancers.

SUMMARY

Accordingly, in one aspect the present disclosure provides a method of treating prostate cancer comprising administering to a patient in need thereof an effective amount of: (i) prostate specific antigen (PSA) peptide PSA 146-154 (SEQ ID NO: 3), and (ii) PSA peptide PSA 154-173 (SEQ ID NO: 1), PSA peptide PSA 210-230 (SEQ ID NO: 2), tumor endothelial marker 8 (TEM8) peptide TEM8 298-306 (SEQ ID NO: 18), or combinations of two or more of the three peptides.

In another aspect, the disclosure provides a composition comprising a fragment of PSA, said fragment peptide comprising the sequence VISNDVCAQVHPQKVTKFML (SEQ ID NO: 1). In another aspect, a composition is provided comprising a fragment of prostate specific antigen (PSA), said fragment peptide comprising the sequence CALPERPSLYTKVVHYRKWIK (SEQ ID NO: 2). In another aspect, the disclosure provides a composition comprising a fragment of TEM8, TEM8 298-306, said fragment peptide comprising the sequence SMNDGLSFI (SEQ ID NO: 18).

In an embodiment, the disclosure provides a method for treating prostate cancer in a human comprising the step of administering a composition of the disclosure to said human in an amount effective to stabilize or reduce serum PSA levels. In some aspects, methods of the disclosure further comprise administrating granulocyte monocyte colony stimulating factor (GM-CSF). In these aspects, said composition and GM-CSF are co-administered, and in further embodiments said composition and GM-CSF are administered concurrently while in still further embodiments said composition and GM-CSF are administered sequentially. In some aspects, said PSA peptide and GM-CSF are co-administered in a weight-to-weight ratio of about 1:5.

The disclosure also provides embodiments in which the PSA and/or TEM8 peptide(s) and GM-CSF are co-administered in multiple injections. In some of these aspects, PSA and/or TEM8 peptide(s) and GM-CSF are co-administered in up to five injections.

In some embodiments, the PSA and/or TEM8 peptide is administered as a composition of dendritic cells pulsed respectively with the PSA and/or TEM8 peptide. In various aspects, a total of about 100 µg PSA peptide is administered in multiple injections.

Administration of a composition or vaccine of the disclosure is, in various aspects, intradermal.

Thus, the disclosure also provides a vaccine comprising: (i) a composition selected from the group consisting of the composition of claim 1, the composition of claim 2 and a composition comprising a prostate specific antigen (PSA) peptide (PSA peptide 146-154; SEQ ID NO: 3), or combinations thereof, and (ii) a pharmaceutically acceptable carrier. In some aspects, the vaccine further comprises granulocyte monocyte colony stimulating factor (GM-CSF). In further aspects, the vaccine further comprises a TLR9 agonist in an amount effective to increase a T cell immune response. In one specific aspect, the TLR9 agonist is a CpG-oligodeoxynucleotide (CpG-ODN).

In further embodiments, the vaccine further comprises an inhibitor of CTLA4 in an amount effective to increase a T cell immune response, and in a specific aspect the inhibitor of CTLA4 is a monoclonal antibody.

In additional embodiments, the vaccine further comprises an inhibitor of PD-1 in an amount effective to increase a T cell immune response. In a specific aspect, the inhibitor of PD-1 is a monoclonal antibody.

The disclosure also provides a method of vaccinating an individual comprising the step of administering a vaccine of the disclosure to the individual in an amount effective to vaccinate the individual. In some aspects, the PSA and/or TEM8 peptide is co-administered with GM-CSF, and in further aspects the PSA and/or TEM8 peptide and GM-CSF are co-administered in multiple injections. In further aspects, the PSA and/or TEM8 peptide and GM-CSF are administered concurrently while in yet further aspects the PSA and/or TEM8 peptide and GM-CSF are administered sequentially. In one aspect, the PSA and/or TEM8 peptide and GM-CSF are co-administered in up to five injections. In a further aspect, a total of about 100 µg PSA and/or TEM8 peptide is administered in multiple injections.

In one embodiment, the PSA and/or TEM8 peptide is administered in weeks 1, 4 and 10, and then every six months up to four years. In another embodiment, the PSA and/or TEM8 peptide is administered in weeks 1, 4 and 10, and then every six months up to four years, wherein an inhibitor of CTLA4 is administered in weeks 1, 4 and 10, and then every eight weeks up until week 52. In a further embodiment, the PSA and/or TEM8 peptide is administered in weeks 1, 4 and 10, and then every six months up to four years, wherein an inhibitor of PD-1 is administered in weeks 1, 4 and 10, and then every eight weeks up until week 52.

In another aspect, the disclosure provides methods of treating cancers other than prostate cancer using TEM8 peptides, TEM8 peptide compositions and/or TEM8 vaccines of the disclosure. The cancers contemplated include any cancer in which it is therapeutically useful to disrupt the vascular supply to the cancer cells. Like the combination of TEM8 peptides with PSA peptides disclosed herein, combination of TEM8 peptides with peptides from tumor associated antigens specific for a particular cancer are is contemplated. For example, TEM8 could be incorporated in peptide-based vaccines for the immunotherapy of various angiogenesis dependent malignancies.

The disclosure also provides a method of identifying a patient that is a candidate for prostate cancer therapy comprising the step of: measuring expression level in a sample from a test individual of one or more genes identified in Table 1 or Table 2 relative to a reference expression level, wherein an increase or a decrease in expression of the genes identified in Table 1 or Table 2 relative to the reference expression level is determinative for identifying whether the patient is a candidate for prostate cancer therapy according to a method of the disclosure. In an aspect, the method further comprises collecting the sample from the test individual. In another aspect, the method further comprises comparing the expression level to the reference expression level.

Accordingly, in some aspects, an increase in expression of a gene selected from the group consisting of 2'-5' oligoadenylate synthetase 1 (OAS1), mitogen-activated protein kinase 1 (MAPK1), Sh2 domain containing 1B (SH2D1B), vannin 1 (VNN1), CD58 molecule (CD58), DEAD box polypeptide 58 (DDX58), X-ray repair complementing defective repair in Chinese hamster cells 4 (XRCC4) and interferon-induced transmembrane protein-3 (IFITM3) is indicative of the patient being a candidate for prostate cancer therapy according to a method of the disclosure.

In further aspects, a decrease in expression of a gene selected from the group consisting of tumor necrosis factor receptor superfamily-member 25 (TNFRSF-25), chemokine C—C motif receptor 7 (CCR7), and phosphoinositide-3-kinase, regulatory subunit 1 alpha (PIK3R1) and epiregulin (EREG) is indicative of the patient being a candidate for prostate cancer therapy according to a method of the disclosure.

In another embodiment, the disclosure provides a method of rendering an individual a candidate for prostate cancer therapy comprising the steps of: (i) modulating expression of at least one gene listed in Table 1 to a degree that renders the individual a candidate for prostate cancer therapy; and (ii) administering a therapeutically effective amount of a composition or vaccine of the disclosure to said patient to treat prostate cancer. In some aspects, modulating increases expression and in one specific aspect the gene is 2'-5' oligoadenylate synthetase 1 (OAS1). In further aspects, modulating decreases expression

TABLE 1

Genes that discriminate among immune responders versus non responders.

| | Parametric p-value | FDR | Permutation p-value | Geom mean of intensities in class 1 | Geom mean of intensities in class 2 | Fold-change | Probe set | Annotations | Gene symbol | Description |
|---|---|---|---|---|---|---|---|---|---|---|
| 1 | 7.70E−05 | 1 | 0.0079365 | 37.04 | 77.38 | 0.48 | 226989 at | Info | RGMB | RGM domain family, member B |
| 2 | 9.44E−05 | 1 | 0.0079365 | 300.96 | 165.39 | 1.82 | 242140 at | Info | NA | NA |
| 3 | 1.04E−04 | 1 | 0.0079365 | 30.62 | 19.31 | 1.59 | 226120 at | Info | TTC8 | tetratricopeptide repeat domain 8 |
| 4 | 2.03E−04 | 1 | 0.015873 | 79.4 | 310.51 | 0.26 | 205767 at | Info | EREG | epiregulin |
| 5 | 2.29E−04 | 1 | 0.0079365 | 261.25 | 167.66 | 1.56 | 242139 s at | Info | NA | NA |
| 6 | 2.74E−04 | 1 | 0.0079365 | 358.97 | 582.01 | 0.62 | 212249 at | Info | PIK3R1 | phosphoinositide-3-kinase, regulatory subunit 1 (alpha) |
| 7 | 3.21E−04 | 1 | 0.015873 | 369.33 | 233.51 | 1.58 | 207181 s at | Info | CASP7 | caspase 7, apoptosis-related cysteine peptidase |
| 8 | 4.12E−04 | 1 | 0.0079365 | 24 | 39.97 | 0.6 | 238577 s at | Info | TSHZ2 | teashirt zinc finger homeobox 2 |
| 9 | 4.42E−04 | 1 | 0.015873 | 71.93 | 37.56 | 1.92 | 235549 at | Info | RNF144B | ring finger protein 144B |
| 10 | 4.58E−04 | 1 | 0.015873 | 87.73 | 130.55 | 0.67 | 214180 at | Info | MAN1C1 | mannosidase, alpha, class 1C, member 1 |
| 11 | 4.66E−04 | 1 | 0.0079365 | 302.66 | 513.53 | 0.59 | 1552634 a at | Info | ZNF101 | zinc finger protein 101 |
| 12 | 4.94E−04 | 1 | 0.0079365 | 29.78 | 16.73 | 1.78 | 220545 s at | Info | TSKS | testis-specific serine kinase substrate |
| 13 | 5.43E−04 | 1 | 0.0079365 | 81.07 | 134.14 | 0.6 | 211721 s at | Info | ZNF551 | zinc finger protein 551 |
| 14 | 5.82E−04 | 1 | 0.0079365 | 836.67 | 337.13 | 2.48 | 205552 s at | Info | OAS1 | 2',5'-oligoadenylate synthetase 1, 40/46 kDa |
| 15 | 5.93E−04 | 1 | 0.0079365 | 251.05 | 404.66 | 0.62 | 227748 at | Info | CCBL2 | cysteine conjugate-beta lyase 2 |
| 16 | 6.02E−04 | 1 | 0.015873 | 149.5 | 96.59 | 1.55 | 218729 at | Info | LXN | latexin |
| 17 | 6.17E−04 | 1 | 0.015873 | 42.28 | 28.51 | 1.48 | 210359 at | Info | MTSS1 | metastasis suppressor 1 |
| 18 | 6.32E−04 | 1 | 0.0079365 | 718.82 | 1067.28 | 0.67 | 208078 s at | Info | NA | NA |
| 19 | 6.44E−04 | 1 | 0.0079365 | 275.9 | 380.02 | 0.73 | 210281 s at | Info | ZMYM2 | zinc finger, MYM-type 2 |
| 20 | 6.69E−04 | 1 | 0.0079365 | 374.69 | 838.19 | 0.45 | 235213 at | Info | NA | NA |
| 21 | 7.14E−04 | 1 | 0.0079365 | 90.55 | 167.69 | 0.54 | 1566448 at | Info | CD6 | CD6 molecule |
| 22 | 8.87E−04 | 1 | 0.015873 | 222.66 | 324.87 | 0.69 | 211282 x at | Info | TNFRSF25 | tumor necrosis factor receptor superfamily, member 25 |
| 23 | 9.59E−04 | 1 | 0.015873 | 4035.16 | 1964.19 | 2.05 | 204006 s at | Info | NA | NA |
| 24 | 9.75E−04 | 1 | 0.0079365 | 70.75 | 23.39 | 3.02 | 219955 at | Info | L1TD1 | LINE-1 type transposase domain containing 1 |
| 25 | 9.95E−04 | 1 | 0.0079365 | 694.23 | 529.76 | 1.31 | 224331 s at | Info | MRPL36 | mitochondrial ribosomal protein L36 |

TABLE 1-continued

Genes that discriminate among immune responders versus non responders.

| | Parametric p-value | FDR | Permutation p-value | Geom mean of intensities in class 1 | Geom mean of intensities in class 2 | Fold-change | Probe set | Annotations | Gene symbol | Description |
|---|---|---|---|---|---|---|---|---|---|---|
| 26 | 1.03E−03 | 1 | 0.015873 | 236.62 | 177.09 | 1.34 | 213526 s at | Info | LIN37 | lin-37 homolog (*C. elegans*) |
| 27 | 1.07E−03 | 1 | 0.015873 | 53.64 | 23.45 | 2.29 | 1554340 a at | Info | C1orf187 | chromosome 1 open reading frame 187 |
| 28 | 1.09E−03 | 1 | 0.0079365 | 1408.76 | 348.23 | 4.05 | 202869 at | Info | OAS1 | 2',5'-oligoadenylate synthetase 1, 40/46 kDa |
| 29 | 1.11E−03 | 1 | 0.015873 | 76.34 | 52.66 | 1.45 | 231396 s at | Info | FAM126A | family with sequence similarity 126, member A |
| 30 | 1.13E−03 | 1 | 0.015873 | 345.08 | 538.14 | 0.64 | 225884 s at | Info | GZF1 | GDNF-inducible zinc finger protein 1 |
| 31 | 1.14E−03 | 1 | 0.0079365 | 45.88 | 61.72 | 0.74 | 229809 at | Info | POU6F1 | POU class 6 homeobox 1 |
| 32 | 1.20E−03 | 1 | 0.0079365 | 66.51 | 106.51 | 0.62 | 225611 at | Info | MAST4 | microtubule associated serine/threonine kinase family member 4 |
| 33 | 1.28E−03 | 1 | 0.015873 | 848.3 | 1377.88 | 0.62 | 200732 s at | Info | PTP4A1 | protein tyrosine phosphatase type IVA, member 1 |
| 34 | 1.31E−03 | 1 | 0.015873 | 1259.08 | 678.25 | 1.86 | 223210 at | Info | CHURC1 | churchill domain containing 1 |
| 35 | 1.34E−03 | 1 | 0.015873 | 301.79 | 448.79 | 0.67 | 230499 at | Info | NA | NA |
| 36 | 1.34E−03 | 1 | 0.0238095 | 91.06 | 55.47 | 1.64 | 210360 s at | Info | MTSS1 | metastasis suppressor 1 |
| 37 | 1.38E−03 | 1 | 0.0079365 | 90.94 | 205.89 | 0.44 | 215592 at | Info | NA | NA |
| 38 | 1.39E−03 | 1 | 0.0238095 | 178.76 | 93.07 | 1.92 | 1553176 at | Info | SH2D1B | SH2 domain containing 1B |
| 39 | 1.42E−03 | 1 | 0.0079365 | 409.74 | 597.37 | 0.69 | 221790 s at | Info | LDLRAP1 | low density lipoprotein receptor adaptor protein 1 |
| 40 | 1.45E−03 | 1 | 0.015873 | 159.23 | 483.35 | 0.33 | 227722 at | Info | RPS23 | ribosomal protein S23 |
| 41 | 1.48E−03 | 1 | 0.0238095 | 2738.12 | 1420.45 | 1.93 | 203037 s at | Info | MTSS1 | metastasis suppressor 1 |
| 42 | 1.49E−03 | 1 | 0.0079365 | 29.54 | 18.28 | 1.62 | 1558508 a at | Info | C1orf53 | chromosome 1 open reading frame 53 |
| 43 | 1.54E−03 | 1 | 0.0079365 | 364.23 | 133.07 | 2.74 | 205844 at | Info | VNN1 | vanin 1 |
| 44 | 1.54E−03 | 1 | 0.015873 | 107.04 | 64.92 | 1.65 | 228058 at | Info | ZG16B | zymogen granule protein 16 homolog B (rat) |
| 45 | 1.54E−03 | 1 | 0.0079365 | 117.12 | 63.86 | 1.83 | 214483 s at | Info | ARFIP1 | ADP-ribosylation factor interacting protein 1 |
| 46 | 1.56E−03 | 1 | 0.015873 | 139.43 | 103.4 | 1.35 | 200856 x at | Info | NA | NA |
| 47 | 1.64E−03 | 1 | 0.0079365 | 128.59 | 89.15 | 1.44 | 1568978 s at | Info | C11orf21 | chromosome 11 open reading frame 21 |
| 48 | 1.67E−03 | 1 | 0.015873 | 73.74 | 57.49 | 1.28 | 222094 at | Info | NA | NA |
| 49 | 1.70E−03 | 1 | 0.0079365 | 7.31 | 9.22 | 0.79 | 239155 at | Info | NA | NA |
| 50 | 1.73E−03 | 1 | 0.0238095 | 472.99 | 56.68 | 8.34 | 206834 at | Info | HBD | hemoglobin, delta |
| 51 | 1.79E−03 | 1 | 0.0079365 | 522.48 | 324.75 | 1.61 | 230352 at | Info | PRPS2 | phosphoribosyl pyrophosphate synthetase 2 |
| 52 | 1.94E−03 | 1 | 0.0079365 | 15.27 | 11.03 | 1.38 | 1558305 at | Info | GIGYF2 | GRB10 interacting GYF protein 2 |
| 53 | 2.03E−03 | 1 | 0.0079365 | 26.82 | 35.45 | 0.76 | 221880 s at | Info | FAM174B | family with sequence similarity 174, member B |
| 54 | 2.06E−03 | 1 | 0.0079365 | 9.78 | 12.39 | 0.79 | 243855 at | Info | NA | NA |
| 55 | 2.10E−03 | 1 | 0.015873 | 153.73 | 236.01 | 0.65 | 211841 s at | Info | TNFRSF25 | tumor necrosis factor receptor superfamily, member 25 |
| 56 | 2.13E−03 | 1 | 0.015873 | 58.87 | 40.13 | 1.47 | 230647 at | Info | TMEM53 | transmembrane protein 53 |
| 57 | 2.14E−03 | 1 | 0.0079365 | 259.79 | 189.98 | 1.37 | 218364 at | Info | LRRFIP2 | leucine rich repeat (in FLII) interacting protein 2 |
| 58 | 2.17E−03 | 1 | 0.0079365 | 43.36 | 66.18 | 0.66 | 1564211 at | Info | C14orf64 | chromosome 14 open reading frame 64 |
| 59 | 2.18E−03 | 1 | 0.0079365 | 224.82 | 610.54 | 0.37 | 209750 at | Info | NR1D2 | nuclear receptor subfamily 1, group D, member 2 |
| 60 | 2.20E−03 | 1 | 0.0079365 | 340.69 | 263.88 | 1.29 | 65591 at | Info | WDR48 | WD repeat domain 48 |
| 61 | 2.22E−03 | 1 | 0.0238095 | 45.98 | 29.41 | 1.56 | 232352 at | Info | ISL2 | ISL LIM homeobox 2 |

TABLE 1-continued

Genes that discriminate among immune responders versus non responders.

| | Parametric p-value | FDR | Permutation p-value | Geom mean of intensities in class 1 | Geom mean of intensities in class 2 | Fold-change | Probe set | Annotations | Gene symbol | Description |
|---|---|---|---|---|---|---|---|---|---|---|
| 62 | 2.24E−03 | 1 | 0.0079365 | 12.81 | 9.86 | 1.3 | 240090 at | Info | NA | NA |
| 63 | 2.31E−03 | 1 | 0.0238095 | 110.96 | 255.3 | 0.43 | 236595 at | Info | NA | NA |
| 64 | 2.35E−03 | 1 | 0.015873 | 2245.36 | 3285.59 | 0.68 | 203408 s at | Info | SATB1 | SATB homeobox 1 |
| 65 | 2.35E−03 | 1 | 0.0238095 | 365.78 | 225.94 | 1.62 | 210422 x at | Info | SLC11A1 | solute carrier family 11 (proton-coupled divalent metal ion transporters), member 1 |
| 66 | 2.39E−03 | 1 | 0.0079365 | 53.09 | 87.67 | 0.61 | 215211 at | Info | LOC730092 | RRN3 RNA polymerase I transcription factor homolog (*S. cerevisiae*) pseudogene |
| 67 | 2.40E−03 | 1 | 0.0079365 | 15.97 | 11.74 | 1.36 | 230657 at | Info | NA | NA |
| 68 | 2.45E−03 | 1 | 0.015873 | 902.08 | 657.71 | 1.37 | 1552264 a at | Info | MAPK1 | mitogen-activated protein kinase 1 |
| 69 | 2.49E−03 | 1 | 0.015873 | 123.26 | 62.52 | 1.97 | 217889 s at | Info | CYBRD1 | cytochrome b reductase 1 |
| 70 | 2.53E−03 | 1 | 0.0079365 | 293.85 | 198.79 | 1.48 | 222157 s at | Info | WDR48 | WD repeat domain 48 |
| 71 | 2.55E−03 | 1 | 0.015873 | 32.07 | 45.19 | 0.71 | 1554929 at | Info | QSK | serine/threonine-protein kinase QSK |
| 72 | 2.56E−03 | 1 | 0.0238095 | 750.18 | 1449.8 | 0.52 | 206337 at | Info | CCR7 | chemokine (C-C motif) receptor 7 |
| 73 | 2.60E−03 | 1 | 0.0079365 | 23.29 | 17.81 | 1.31 | 222680 s at | Info | DTL | denticleless homolog (*Drosophila*) |
| 74 | 2.61E−03 | 1 | 0.0079365 | 904.27 | 1492.2 | 0.61 | 200965 s at | Info | ABLIM1 | actin binding LIM protein 1 |
| 75 | 2.67E−03 | 1 | 0.0079365 | 205.99 | 99.24 | 2.08 | 207500 at | Info | CASP5 | caspase 5, apoptosis-related cysteine peptidase |
| 76 | 2.67E−03 | 1 | 0.0238095 | 113.92 | 188.55 | 0.6 | 1562731 s at | Info | MDS2 | myelodysplastic syndrome 2 translocation associated |
| 77 | 2.69E−03 | 1 | 0.0079365 | 169.46 | 238.58 | 0.71 | 239388 at | Info | NA | NA |
| 78 | 2.70E−03 | 1 | 0.015873 | 19.33 | 33.29 | 0.58 | 230552 at | Info | NA | NA |
| 79 | 2.82E−03 | 1 | 0.0238095 | 146.54 | 249.67 | 0.59 | 228109 at | Info | RASGRF2 | Ras protein-specific guanine nucleotide-releasing factor 2 |
| 80 | 2.90E−03 | 1 | 0.0079365 | 16.49 | 12.92 | 1.28 | 208552 at | Info | GRIK4 | glutamate receptor, ionotropic, kainate 4 |
| 81 | 2.90E−03 | 1 | 0.0079365 | 40.81 | 27.18 | 1.5 | 241841 at | Info | NA | NA |
| 82 | 2.91E−03 | 1 | 0.015873 | 23.21 | 17.74 | 1.31 | 236477 at | Info | PRPF40A | PRP40 pre-mRNA processing factor 40 homolog A (*S. cerevisiae*) |
| 83 | 2.92E−03 | 1 | 0.015873 | 628.01 | 430.35 | 1.46 | 216942 s at | Info | CD58 | CD58 molecule |
| 84 | 2.93E−03 | 1 | 0.0079365 | 33.75 | 46.41 | 0.73 | 236260 at | Info | NA | NA |
| 85 | 2.95E−03 | 1 | 0.0079365 | 23.66 | 17.2 | 1.38 | 240661 at | Info | LOC284475 | hypothetical protein LOC284475 |
| 86 | 2.96E−03 | 1 | 0.015873 | 36.58 | 50.07 | 0.73 | 235616 at | Info | TSHZ2 | teashirt zinc finger homeobox 2 |
| 87 | 2.97E−03 | 1 | 0.0238095 | 122.86 | 182.12 | 0.67 | 201829 at | Info | NET1 | neuroepithelial cell transforming 1 |
| 88 | 2.99E−03 | 1 | 0.015873 | 37.55 | 27.91 | 1.35 | 227055 at | Info | METTL7B | methyltransferase like 7B |
| 89 | 2.99E−03 | 1 | 0.0238095 | 411.65 | 662.69 | 0.62 | 227867 at | Info | LOC129293 | hypothetical protein LOC129293 |
| 90 | 2.99E−03 | 1 | 0.0079365 | 20.5 | 15.49 | 1.32 | 215150 at | Info | YOD1 | YOD1 OTU deubiquinating enzyme 1 homolog (*S. cerevisiae*) |
| 91 | 3.04E−03 | 1 | 0.0079365 | 119.84 | 92.21 | 1.3 | 236449 at | Info | NA | NA |
| 92 | 3.06E−03 | 1 | 0.015873 | 46.85 | 75.85 | 0.62 | 229497 at | Info | ANKDD1A | ankyrin repeat and death domain containing 1A |
| 93 | 3.07E−03 | 1 | 0.0079365 | 199.75 | 144.67 | 1.38 | 204001 at | Info | SNAPC3 | small nuclear RNA activating complex, polypeptide 3, 50 kDa |
| 94 | 3.09E−03 | 1 | 0.0079365 | 58.07 | 45.73 | 1.27 | 230633 at | Info | TMEM102 | transmembrane protein 102 |
| 95 | 3.10E−03 | 1 | 0.0238095 | 447.63 | 317.35 | 1.41 | 203583 at | Info | UNC50 | unc-50 homolog (*C. elegans*) |

TABLE 1-continued

Genes that discriminate among immune responders versus non responders.

| | Parametric p-value | FDR | Permutation p-value | Geom mean of intensities in class 1 | Geom mean of intensities in class 2 | Fold-change | Probe set | Annotations | Gene symbol | Description |
|---|---|---|---|---|---|---|---|---|---|---|
| 96 | 3.13E−03 | 1 | 0.0079365 | 359.02 | 966.16 | 0.37 | 219228 at | Info | ZNF331 | zinc finger protein 331 |
| 97 | 3.15E−03 | 1 | 0.015873 | 9.92 | 13.61 | 0.73 | 1570357 at | Info | STX8 | syntaxin 8 |
| 98 | 3.19E−03 | 1 | 0.0238095 | 1316.13 | 1969.6 | 0.67 | 226905 at | Info | FAM101B | family with sequence similarity 101, member B |
| 99 | 3.20E−03 | 1 | 0.015873 | 1270.49 | 861.04 | 1.48 | 205173 x at | Info | CD58 | CD58 molecule |
| 100 | 3.21E−03 | 1 | 0.015873 | 30.11 | 21.04 | 1.43 | 221149 at | Info | GPR77 | G protein-coupled receptor 77 |
| 101 | 3.22E−03 | 1 | 0.015873 | 37.21 | 61.72 | 0.6 | 207926 at | Info | GP5 | glycoprotein V (platelet) |
| 102 | 3.23E−03 | 1 | 0.015873 | 328.75 | 608.37 | 0.54 | 204642 at | Info | S1PR1 | sphingosine-1-phosphate receptor 1 |
| 103 | 3.25E−03 | 1 | 0.015873 | 359.63 | 243.41 | 1.48 | 226668 at | Info | WDSUB1 | WD repeat, sterile alpha motif and U-box domain containing 1 |
| 104 | 3.28E−03 | 1 | 0.0079365 | 796.74 | 553.15 | 1.44 | 55692 at | Info | ELMO2 | engulfment and cell motility 2 |
| 105 | 3.30E−03 | 1 | 0.0079365 | 33.73 | 26.11 | 1.29 | 225018 at | Info | SPIRE1 | spire homolog 1 (Drosophila) |
| 106 | 3.32E−03 | 1 | 0.015873 | 835.14 | 564.8 | 1.48 | 226673 at | Info | SH2D3C | SH2 domain containing 3C |
| 107 | 3.36E−03 | 1 | 0.0079365 | 15.48 | 10.01 | 1.55 | 230399 at | Info | NA | NA |
| 108 | 3.36E−03 | 1 | 0.015873 | 48.7 | 82.54 | 0.59 | 1559097 at | Info | C14orf64 | chromosome 14 open reading frame 64 |
| 109 | 3.36E−03 | 1 | 0.015873 | 16.35 | 22.57 | 0.72 | 233416 at | Info | NA | NA |
| 110 | 3.41E−03 | 1 | 0.015873 | 219.39 | 111.28 | 1.97 | 218701 at | Info | LACTB2 | lactamase, beta 2 |
| 111 | 3.42E−03 | 1 | 0.0079365 | 51.87 | 29.7 | 1.75 | 234994 at | Info | TMEM200A | transmembrane protein 200A |
| 112 | 3.42E−03 | 1 | 0.015873 | 198.89 | 97.52 | 2.04 | 239740 at | Info | ETV6 | ets variant 6 |
| 113 | 3.42E−03 | 1 | 0.015873 | 216.78 | 306.86 | 0.71 | 223007 s at | Info | C9orf5 | chromosome 9 open reading frame 5 |
| 114 | 3.44E−03 | 1 | 0.0238095 | 587.73 | 389.98 | 1.51 | 221735 at | Info | WDR48 | WD repeat domain 48 |
| 115 | 3.45E−03 | 1 | 0.015873 | 11.01 | 8.61 | 1.28 | 214967 at | Info | NA | NA |
| 116 | 3.48E−03 | 1 | 0.0079365 | 21.49 | 15.44 | 1.39 | 237054 at | Info | ENPP5 | ectonucleotide pyrophosphatase/ phosphodiesterase 5 (putative function) |
| 117 | 3.60E−03 | 1 | 0.015873 | 170.12 | 126.15 | 1.35 | 225686 at | Info | SKA2 | spindle and kinetochore associated complex subunit 2 |
| 118 | 3.62E−03 | 1 | 0.015873 | 284.46 | 156.6 | 1.82 | 218943 s at | Info | DDX58 | DEAD (Asp-Glu-Ala-Asp) box polypeptide 58 |
| 119 | 3.65E−03 | 1 | 0.0079365 | 56.45 | 74.21 | 0.76 | 239925 at | Info | NA | NA |
| 120 | 3.73E−03 | 1 | 0.015873 | 26.97 | 43.06 | 0.63 | 212096 s at | Info | MTUS1 | mitochondrial tumor suppressor 1 |
| 121 | 3.74E−03 | 1 | 0.0079365 | 215.46 | 278.87 | 0.77 | 208614 s at | Info | FLNB | filamin B, beta |
| 122 | 3.74E−03 | 1 | 0.0079365 | 74.79 | 128.89 | 0.58 | 1569652 at | Info | MLLT3 | myeloid/lymphoid or mixed-lineage leukemia (trithorax homolog, Drosophila); translocated to, 3 |
| 123 | 3.77E−03 | 1 | 0.0079365 | 123.98 | 172.07 | 0.72 | 228661 s at | Info | NA | NA |
| 124 | 3.81E−03 | 1 | 0.0079365 | 117.49 | 85.23 | 1.38 | 210813 s at | Info | XRCC4 | X-ray repair complementing defective repair in Chinese hamster cells 4 |
| 125 | 3.82E−03 | 1 | 0.0079365 | 254.06 | 177.02 | 1.44 | 200979 at | Info | PDHA1 | pyruvate dehydrogenase (lipoamide) alpha 1 |
| 126 | 3.85E−03 | 1 | 0.015873 | 353.79 | 264.67 | 1.34 | 218049 s at | Info | MRPL13 | mitochondrial ribosomal protein L13 |
| 127 | 3.92E−03 | 1 | 0.0079365 | 15.9 | 10.75 | 1.48 | 241981 at | Info | FAM20A | family with sequence similarity 20, member A |
| 128 | 3.92E−03 | 1 | 0.0238095 | 598.3 | 391.96 | 1.53 | 1552263 at | Info | MAPK1 | mitogen-activated protein kinase 1 |
| 129 | 4.05E−03 | 1 | 0.0238095 | 51.97 | 89.58 | 0.58 | 227984 at | Info | LOC650392 | hypothetical protein LOC650392 |

TABLE 1-continued

Genes that discriminate among immune responders versus non responders.

| | Parametric p-value | FDR | Permutation p-value | Geom mean of intensities in class 1 | Geom mean of intensities in class 2 | Fold-change | Probe set | Annotations | Gene symbol | Description |
|---|---|---|---|---|---|---|---|---|---|---|
| 130 | 4.06E−03 | 1 | 0.0238095 | 115.3 | 60.53 | 1.9 | 214510_at | Info | GPR20 | G protein-coupled receptor 20 |
| 131 | 4.07E−03 | 1 | 0.0079365 | 198.49 | 252.6 | 0.79 | 213254_at | Info | TNRC6B | trinucleotide repeat containing 6B |
| 132 | 4.09E−03 | 1 | 0.015873 | 426.34 | 323.59 | 1.32 | 203714_s_at | Info | TBCE | tubulin folding cofactor E |
| 133 | 4.18E−03 | 1 | 0.0079365 | 217.89 | 162.17 | 1.34 | 215923_s_at | Info | PSD4 | pleckstrin and Sec7 domain containing 4 |
| 134 | 4.19E−03 | 1 | 0.0238095 | 19762.36 | 4524.98 | 4.37 | 214414_x_at | Info | NA | NA |
| 135 | 4.19E−03 | 1 | 0.0079365 | 42.74 | 31.8 | 1.34 | 229671_s_at | Info | C21orf45 | chromosome 21 open reading frame 45 |
| 136 | 4.20E−03 | 1 | 0.0079365 | 7.6 | 9.73 | 0.78 | 213992_at | Info | COL4A6 | collagen, type IV, alpha 6 |
| 137 | 4.21E−03 | 1 | 0.0238095 | 202.26 | 320.5 | 0.63 | 239122_at | Info | NA | NA |
| 138 | 4.22E−03 | 1 | 0.0238095 | 27.86 | 43.11 | 0.65 | 1559413_at | Info | TCP11L2 | t-complex 11 (mouse)-like 2 |
| 139 | 4.24E−03 | 1 | 0.015873 | 337.46 | 236.59 | 1.43 | 207765_s_at | Info | KIAA1539 | KIAA1539 |
| 140 | 4.27E−03 | 1 | 0.015873 | 112.75 | 83.24 | 1.35 | 201714_at | Info | TUBG1 | tubulin, gamma 1 |
| 141 | 4.31E−03 | 1 | 0.0238095 | 188.6 | 107.85 | 1.75 | 228619_x_at | Info | TIPRL | TIP41, TOR signaling pathway regulator-like (*S. cerevisiae*) |
| 142 | 4.31E−03 | 1 | 0.0079365 | 1241.97 | 980.99 | 1.27 | 202266_at | Info | TTRAP | TRAF and TNF receptor associated protein |
| 143 | 4.35E−03 | 1 | 0.015873 | 78.83 | 58.94 | 1.34 | 217777_s_at | Info | PTPLAD1 | protein tyrosine phosphatase-like A domain containing 1 |
| 144 | 4.36E−03 | 1 | 0.015873 | 182.1 | 71.78 | 2.54 | 207194_s_at | Info | ICAM4 | intercellular adhesion molecule 4 (Landsteiner-Wiener blood group) |
| 145 | 4.36E−03 | 1 | 0.0238095 | 515.45 | 273.23 | 1.89 | 222453_at | Info | CYBRD1 | cytochrome b reductase 1 |
| 146 | 4.37E−03 | 1 | 0.0079365 | 10.32 | 8.16 | 1.27 | 206950_at | Info | SCN9A | sodium channel, voltage-gated, type IX, alpha subunit |
| 147 | 4.38E−03 | 1 | 0.0238095 | 1359.8 | 732.09 | 1.86 | 210423_s_at | Info | SLC11A1 | solute carrier family 11 (proton-coupled divalent metal ion transporters), member 1 |
| 148 | 4.39E−03 | 1 | 0.0238095 | 55.91 | 118.03 | 0.47 | 204749_at | Info | NAP1L3 | nucleosome assembly protein 1-like 3 |
| 149 | 4.40E−03 | 1 | 0.015873 | 59.77 | 44.49 | 1.34 | 233812_at | Info | NCRNA00028 | non-protein coding RNA 28 |
| 150 | 4.43E−03 | 1 | 0.015873 | 9.42 | 7.55 | 1.25 | 223599_at | Info | TRIM6 | tripartite motif-containing 6 |
| 151 | 4.44E−03 | 1 | 0.015873 | 97.29 | 70.87 | 1.37 | 225521_at | Info | ANAPC7 | anaphase promoting complex subunit 7 |
| 152 | 4.48E−03 | 1 | 0.015873 | 430.63 | 551.21 | 0.78 | 225077_at | Info | CHD2 | chromodomain helicase DNA binding protein 2 |
| 153 | 4.51E−03 | 1 | 0.015873 | 256.45 | 381.11 | 0.67 | 1552633_at | Info | ZNF101 | zinc finger protein 101 |
| 154 | 4.53E−03 | 1 | 0.0079365 | 692.3 | 1047.21 | 0.66 | 225262_at | Info | FOSL2 | FOS-like antigen 2 |
| 155 | 4.54E−03 | 1 | 0.031746 | 14763.3 | 2292.73 | 6.44 | 211699_x_at | Info | NA | NA |
| 156 | 4.54E−03 | 1 | 0.0238095 | 17.16 | 23.98 | 0.72 | 205372_at | Info | PLAG1 | pleiomorphic adenoma gene 1 |
| 157 | 4.58E−03 | 1 | 0.015873 | 10.41 | 13.45 | 0.77 | 236952_at | Info | NA | NA |
| 158 | 4.60E−03 | 1 | 0.0238095 | 8355.56 | 5403.36 | 1.55 | 212203_x_at | Info | IFITM3 | interferon induced transmembrane protein 3 (1-8U) |
| 159 | 4.64E−03 | 1 | 0.015873 | 54.15 | 70.03 | 0.77 | 243111_at | Info | NA | NA |
| 160 | 4.66E−03 | 1 | 0.0238095 | 158.5 | 245.54 | 0.65 | 204143_s_at | Info | ENOSF1 | enolase superfamily member 1 |
| 161 | 4.67E−03 | 1 | 0.0079365 | 18.25 | 14.56 | 1.25 | 206726_at | Info | HPGDS | hematopoietic prostaglandin D synthase |
| 162 | 4.69E−03 | 1 | 0.031746 | 99.31 | 217.27 | 0.46 | 233127_at | Info | NA | NA |
| 163 | 4.71E−03 | 1 | 0.015873 | 137.76 | 196.03 | 0.7 | 226528_at | Info | MTX3 | metaxin 3 |
| 164 | 4.89E−03 | 1 | 0.0238095 | 68.88 | 96.12 | 0.72 | 201596_x_at | Info | KRT18 | keratin 18 |

TABLE 1-continued

Genes that discriminate among immune responders versus non responders.

| | Parametric p-value | FDR | Permutation p-value | Geom mean of intensities in class 1 | Geom mean of intensities in class 2 | Fold-change | Probe set | Annotations | Gene symbol | Description |
|---|---|---|---|---|---|---|---|---|---|---|
| 165 | 4.93E−03 | 1 | 0.0079365 | 148.97 | 113.18 | 1.32 | 230279 at | Info | NA | NA |
| 166 | 4.93E−03 | 1 | 0.0079365 | 716.09 | 572.6 | 1.25 | 201725 at | Info | CDC123 | cell division cycle 123 homolog (S. cerevisiae) |

'Observed v. Expected' Table of GO Classes and Parent Classes, in List of 166 Genes Shown Above:

Only GO classes and parent classes with at least 5 observations in the selected subset and with an 'Observed vs. Expected' ratio of at least 2 are shown.

Cellular Component

| GO ID | GO Term | Observed in selected subset | Expected in selected subset | Observed/ Expected |
|---|---|---|---|---|
| GO:0030659 | cytoplasmic vesicle membrane | 5 | 0.75 | 6.64 |
| GO:0012506 | vesicle membrane | 5 | 0.82 | 6.07 |
| GO:0044433 | cytoplasmic vesicle part | 5 | 1.03 | 4.85 |
| GO:0005815 | microtubule organizing center | 7 | 1.82 | 3.85 |
| GO:0005840 | ribosome | 6 | 2.28 | 2.63 |

Molecular Function

| GO ID | GO Term | Observed in selected subset | Expected in selected subset | Observed/ Expected |
|---|---|---|---|---|
| GO:0005085 | guanyl-nucleotide exchange factor activity | 6 | 1.32 | 4.54 |
| GO:0043565 | sequence-specific DNA binding | 7 | 3.22 | 2.18 |
| GO:0030695 | GTPase regulator activity | 7 | 3.32 | 2.11 |
| GO:0060589 | nucleoside-triphosphatase regulator activity | 7 | 3.38 | 2.07 |

Biological Process

| GO ID | GO Term | Observed in selected subset | Expected in selected subset | Observed/ Expected |
|---|---|---|---|---|
| GO:0007265 | Ras protein signal transduction | 7 | 2.2 | 3.18 |
| GO:0007626 | locomotory behavior | 6 | 1.93 | 3.11 |
| GO:0007169 | transmembrane receptor protein tyrosine kinase signaling pathway | 6 | 2.08 | 2.89 |
| GO:0051056 | regulation of small GTPase mediated signal transduction | 5 | 1.83 | 2.74 |
| GO:0008284 | positive regulation of cell proliferation | 6 | 2.56 | 2.35 |
| GO:0030182 | neuron differentiation | 8 | 3.46 | 2.31 |
| GO:0007010 | cytoskeleton organization | 9 | 3.92 | 2.3 |
| GO:0048699 | generation of neurons | 9 | 4.18 | 2.15 |
| GO:0002520 | immune system development | 7 | 3.33 | 2.1 |

DETAILED DESCRIPTION OF THE INVENTION

Definitions

Figure 1:
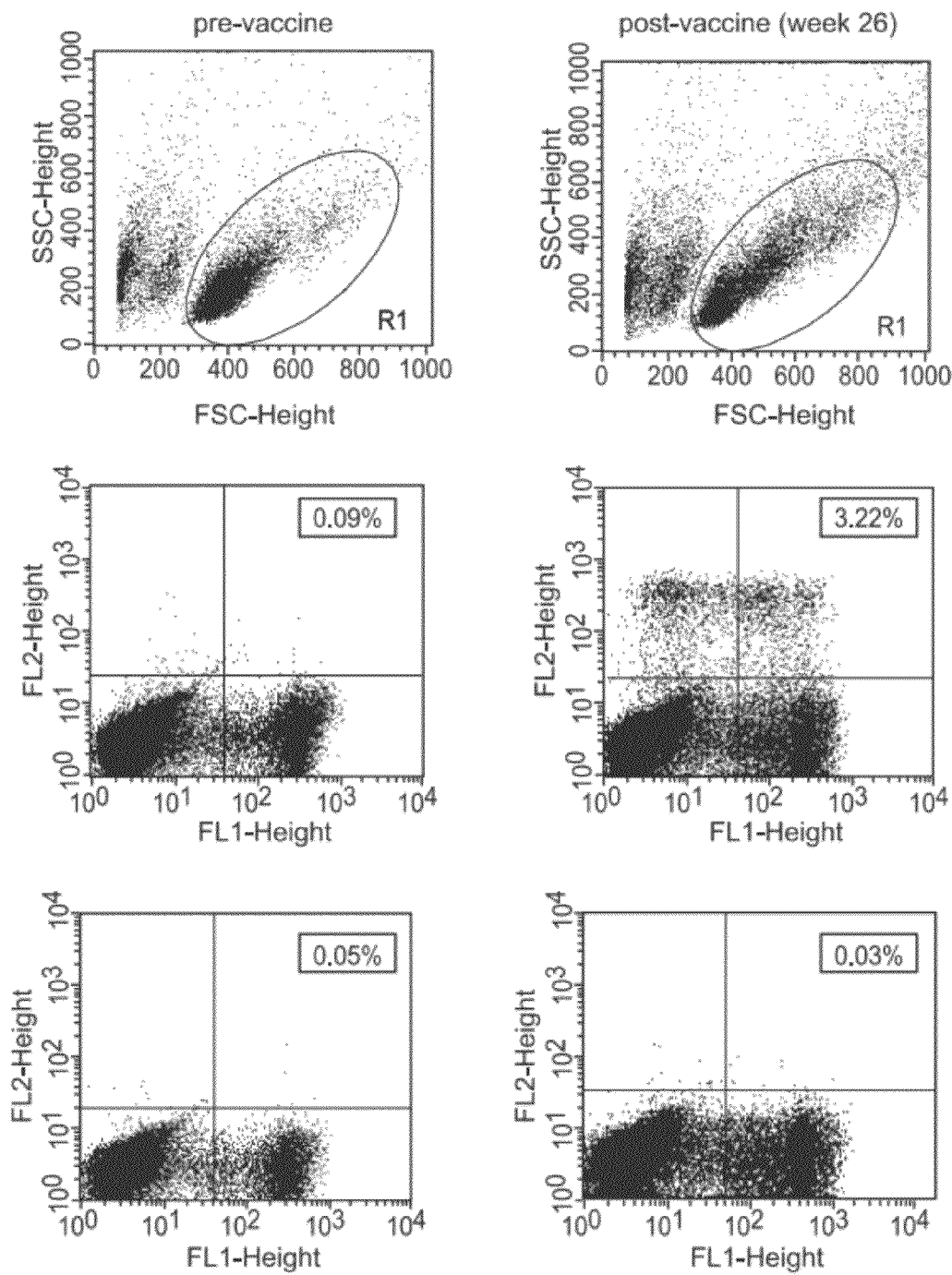
FIG. 1 depicts representative flow cytometric data showing the detection of CD8+ PSA146-154 peptide-tetramer+ cells in patient UPIN28. PBMC were sensitized in vitro with PSA146-154 peptide for 3 cycles and resulting T-cells were doubly stained with PSA146-154 peptide-tetramer-PE (middle panel, FL2) or negative control tetramer-PE (lower panel, FL2) and CD8-FITC (lower panel and middle, FL1). A greater number of CD8+ PSA146-154 peptide-tetramer+ cells (upper right quadrants) were observed on post-vaccine compared to pre-vaccine samples.

The terms "effective amount" or "therapeutically effective amount," as used herein, refer to an amount of a compound sufficient to treat, ameliorate, or prevent prostate cancer, or to exhibit a detectable therapeutic, prophylactic, or inhibitory effect. The effect can be detected by, for example, an improvement in clinical prostate cancer, or reduction in symptoms associated with prostate cancer. The precise effective amount for a subject will depend upon the subject's body weight, size, and health; the nature and extent of the condition; and the therapeutic or combination of therapeutics selected for administration. Where a drug has been approved by the U.S. Food and Drug Administration (FDA) or a foreign counterpart agency, a "therapeutically effective amount" refers to the dosage approved by the FDA or its counterpart foreign agency for treatment of the identified disease or condition.

As used herein, a patient "in need thereof" is a patient who would benefit from administration of a composition of the disclosure. The patient may be suffering from any disease or condition for which a composition of the disclosure may be useful in ameliorating symptoms. In various aspects, the patient is a patient diagnosed with prostate cancer.

As used herein, "co-administration" is understood to include concurrent administration and sequential administration. Thus, the terms are understood to encompass administration simultaneously, or at different times, and by the same route or by different routes, as long as the two agents are given in a manner that allows both agents to be affecting the body at the same time.

"Sequential administration" as used herein is understood to mean one of the compounds or agents is given first followed by the second. When administered sequentially, the combination may be administered in two or more administrations.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, dyes and combinations thereof, as would be known to one of ordinary skill in the art (see, for example and without limitation, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

"Vaccine" as used herein can be either a therapeutic vaccine or a prophylactic vaccine. A prophylactic vaccine is understood to be a composition that is administered to a healthy individual to prevent a disease. A therapeutic vaccine is administered to an individual that already has a disease in order to alleviate or eliminate the disease.

Compositions/Vaccines

It is an aim of the present disclosure to provide compositions and vaccines for treating or preventing prostate cancer. Thus, PSA peptides and TEM8 peptides are provided herein that are contemplated for administration to a human. In various embodiments, the PSA peptide(s) are administered: (i) alone; (ii) with an additional agent (biologic or chemical); (iii) in a composition of dendritic cells that have been pulsed with the PSA peptide(s); (iv) with a delivery vector; (v) with an immunomodulating adjuvant; and (vi) as part of a vaccine composition. In various embodiments, the TEM8 peptide(s) are administered: (i) alone; (ii) with an additional agent (biologic or chemical); (iii) in a composition of dendritic cells that have been pulsed with the TEM8 peptide(s); (iv) with a delivery vector; (v) with an immunomodulating adjuvant; and (vi) as part of a vaccine composition.

Accordingly, in various embodiments the disclosure provides a composition comprising a fragment of prostate specific antigen (PSA), said fragment peptide comprising the sequence VISNDVCAQVHPQKVTKFML (SEQ ID NO: 1). In various aspects, a composition is provided comprising a fragment of prostate specific antigen (PSA), said fragment peptide consisting of the sequence VISNDVCAQVHPQKVTKFML (SEQ ID NO: 1). In various aspects, a composition is provided comprising a fragment of prostate specific antigen (PSA), said fragment peptide consisting essentially of the sequence VISNDVCAQVHPQKVTKFML (SEQ ID NO: 1). In further aspects, the PSA peptide(s) are administered: (i) alone; (ii) with a delivery vector; (iii) with an immunomodulating adjuvant; (iv) with additional biologic agent or chemical; (v) in a composition of dendritic cells that have been pulsed with the PSA peptide(s); and (vi) as part of a vaccine composition.

In various embodiments, a composition is provided comprising a fragment of prostate specific antigen (PSA), said fragment peptide comprising the sequence CALPERPSLYTKVVHYRKWIK (SEQ ID NO: 2). In various aspects, a composition is provided comprising a fragment of prostate specific antigen (PSA), said fragment peptide consisting of the sequence CALPERPSLYTKVVHYRKWIK (SEQ ID NO: 2). In various aspects, a composition is provided comprising a fragment of prostate specific antigen (PSA), said fragment peptide consisting essentially of the sequence CALPERPSLYTKVVHYRKWIK (SEQ ID NO: 2). In further aspects, the PSA peptide(s) are administered: (i) alone; (ii) with a delivery vector; (iii) with an immunomodulating adjuvant; (iv) with additional biologic agent or chemical; (v) in a composition of dendritic cells that have been pulsed with the PSA peptide(s); and (vi) as part of a vaccine composition.

In various embodiments, a composition is provided comprising a fragment of TEM8, said fragment peptide comprising the sequence SMNDGLSFI (SEQ ID NO: 18). In various aspects, a composition is provided comprising a fragment of TEM8, said fragment peptide consisting of the sequence SMNDGLSFI (SEQ ID NO: 18). In various aspects, a composition is provided comprising a fragment of TEM8, said fragment peptide consisting essentially of the sequence SMNDGLSFI (SEQ ID NO: 18). In further aspects, the PSA peptide(s) are administered: (i) alone; (ii) with a delivery vector; (iii) with an immunomodulating adjuvant; (iv) with additional biologic agent or chemical; (v) in a composition of dendritic cells that have been pulsed with the PSA peptide(s); and (vi) as part of a vaccine composition.

In various embodiments, the disclosure provides a vaccine comprising: (i) a composition of the disclosure or combinations thereof, and (ii) a pharmaceutically acceptable carrier. In one aspect, the vaccine comprises PSA peptide 146-154 (SEQ ID NO: 3). In various aspects, the vaccine further comprises PSA peptide PSA 154-173 (SEQ ID NO: 1), PSA peptide PSA 210-230 (SEQ ID NO: 2), tumor endothelial marker 8 (TEM8) peptide TEM8 298-306 (SEQ ID NO: 18), or combinations of two or more of the three peptides with the PSA peptide 146-154 (SEQ ID NO: 3). In various aspects, the vaccine further comprises GM-CSF.

In various embodiments, the vaccine further comprises a Toll-like receptor 9 (TLR9) agonist. In one aspect, the TLR9 agonist is a CpG-oligodeoxynucleotide (CpG-ODN).

In various embodiments, the vaccine further comprises an inhibitor of Cytotoxic T-Lymphocyte Antigen 4 (CTLA4) in an amount effective to increase a T cell immune response. In a specific aspect, the inhibitor of CTLA4 is a monoclonal antibody.

In various embodiments, the disclosure provides a vaccine that further comprises an inhibitor of Programmed Death 1 (PD-1) in an amount effective to increase a T cell immune response. In various embodiments, the inhibitor of PD-1 is a monoclonal antibody.

PSA and TEM8 peptides disclosed herein are contemplated for use in compositions to be administered according to the methods described below. It is specifically contemplated that peptides can vary in length or sequence from those specifically described herein and still retain their functional characteristics necessary for use in the invention. Also contemplated for use are, for example, allelic variants, conservative substitution variants and homologs that can be isolated/generated and characterized without undue experimentation following the methods outlined below.

Conservative amino acid substitutions can frequently be made in a protein or peptide without altering either the conformation or the function of the protein or peptide. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example and without limitation, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant.

Fusion proteins are made by techniques well known to a person skilled in the art, such as by linking the PSA and/or TEM8 peptide of the disclosure with other recombinant peptides or proteins. There is no restriction as to the peptides or proteins fused to the peptide of the present disclosure. Non-limiting examples of fusion proteins contemplated by the disclosure include PSA peptide(s) coated onto a microbead or microsphere and PSA peptide(s) incorporated into a liposome.

Compositions/vaccines, in various embodiments, comprise one or more PSA and/or TEM8 peptides as disclosed herein formulated, combined, mixed, incorporated into and/or matrixed with one or more adjuvants, diluents, carriers and the like that is administered to a subject by any suitable route to induce protective and/or ameliorative immune responses to the PSA and/or TEM8 peptide. "Adjuvant" refers to any substance that is distinct from the PSA or TEM8 peptide which when incorporated into a composition acts generally to accelerate, prolong, enhance, augment and/or potentiate the host's immune response to the PSA or TEM8 peptide, and includes compositions encompassed by the terms immunomodulator, immunopotentiator and immunoenhancer. In general, adjuvants comprise a heterogeneous group of compounds broadly classified as oil emulsions, mineral compounds, bacterial products, liposomes and immunostimulating complexes (IS-COMs).

Exemplary adjuvants include without limitation, ADJUMER™ (polyphosphazene); aluminum phosphate gel; algal glucans; algammulin; aluminum hydroxide gel (alum); high protein adsorbency aluminum hydroxide gel; low viscosity aluminum hydroxide gel; AF or SPT (emulsion of squalane (5%), Tween 80(0.2%), Pluronic L121(1.25%), phosphate-buffered saline pH 7.4); AVRIDIE™ (propanediamine); BAY R1005™ ((N-(2-Deoxy-2-L-leucylamino-b-D-glucopyranosyl)-N-octadecyldod-ecanoylamide hydroacetate); CALCITRIOL™ (1α, 25-dihydroxyvitamin D3); calcium phosphate gel; CAP™ (calcium phosphate nanoparticles); cholera holotoxin, cholera toxin A1-protein A-D fragment fusion protein, cholera toxin B subunit; CRL 1005 (Block Copolymer P1205); cytokine containing liposomes; DDA (dimethyldioctadecylammonium bromide); DHEA (dehydroepiandrosterone); DMPC (dimyristoyl phosphatidylcholine); DMPG (dimyristoyl phosphatidylglycerol); DOC/Alum Complex (Deoxycholic Acid Sodium Salt); Freund's Complete Adjuvant; Freund's Incomplete Adjuvant; Gamma Inulin; Gerbu Adjuvant (mixture of: i) N-Acetylglucosaminyl-(P1-4)-N-acetylmuramyl-L-alanyl-D-glutamine (GMDP), ii) Dimethyl dioctadecylammonium. chloride (DDA), iii) Zinc L-proline salt complex (ZnPro-8); GM-CSF; GMDP (N-acetylglucosaminyl-(b1-4)—N-acetylmuramyl-L-al-anyl-D-isoglutamine); IC31™; Imiquimod (1-(2-methypropyl)-IH-imidazo[4,5-c]quinol-in-4-amine); ImmTher™ (N-acetylglucosaminyl-N-acetyhnuramyl-L-Ala-D-iso-Glu-L-Ala-glycerol dipalmitate); DRVs (Immunoliposomes prepared from Dehydration-Rehyrdation Vesicles); Interferon-.gamma.; Interleukin-1.beta.; Interleukin-2; Interleukin-7; Interleukin-12; ISCOMS™ (Immune Stimulating Complexes); ISCOPREP 7.0.3.™; Liposomes; LOXORIBINE™ (7-allyl-8-oxoguanosine); LT Oral Adjuvant™ (*E. coli* labile enterotoxin protoxin); Microspheres and Microparticles of any composition; MF59™; (squalene.water emulsion); MONTANIDE ISA 51™ (purified Incomplete Freund's Adjuvant); MONTANIDE ISA 720™ (metabolizable oil adjuvant); MPL™ (3-Q-desacyl-4'-monophosphoryl lipid A); MTP-PE and MTP-PE liposomes ((N-acetyl-L-alanyl-D-isoglutaminyl-1-L-alanine-2-(1,2-dipalmitoyl-sn-glycero-3-(hydroxy-phosphoryloxy)) ethylamide, mono sodium salt); MURAMETIDE™ (Nac-Mur-L-Ala-D-Gln-OCH3); MURAPALMITINE™ and D-MURAPALMITINE™ (Nac-Mur-L-Thr-D-isoGIn-sn-glyc-erol dipalmitoyl); NAGO (Neuraminidase-galactose oxidase); Nanospheres or Nanoparticles of any composition; NISVs (Non-Ionic Surfactant Vesicles); PLEURAN™ (.beta.-glucan); PLGA, PGA and PLA (homo- and co-polymers of lactic and glycolic acid; micro-/nanospheres); PLURONIC L121™; PMMA (polymethyl methacrylate); PODDS™ (oroteinoid microspheres); Polyethylene carbamate derivatives; Poly rA:Poly rU (Polyadenylic acid-poly-uridylic acid complex); Polysorbate 80 (Tween 80); Protein Cochleates (Avanti Polar Lipids, Inc., Alabaster, Ala.); STIMULON™ (QS-21); Quil-A (Quil-A saponin); S-28463 (4-Amino-otec,-dimethyl-2-ethox-ymethyl-1H-imidazo[4,5-c]quinoline-1-ethanol); SAF-1™ (Syntex Adjuvant Formulation); Sendai proteoliposomes and Sendai-containing lipid matrices; Span-85 (sorbitan trioleate); Specol (emulstion of Marcol 52, Span 85 and Tween 85); Squalene or Robane® (2,6,10,15,19,23-hexamethyl-ltetracosane and 2,6,10,15,19,23-hexamethyl-2,6,10,14,18,22 tetracosahexaene); Stearyl Tyrosine (Octadecyl tyrosine hydrochloride); Theramide® (N-acetylglucosaminyl-N-acetylinuramyl-L-Ala-D-isoGlu-L-Al-a-dipalmitoxy propylamide); Theronyl-MDP (Termurtide™ or [thr 1]-MDP; N-acetyl muramyl-L-threonyl-D-isoglutamine); Ty Particles (Ty-VLPs or virus like particles); Walter Reed Liposomes (Liposomes containing lipid A adsorbed to aluminum hydroxide).

In further embodiments, PSA and/or TEM8 peptide(s) are administered with a delivery vector. As used herein, a delivery vector is any vector that comprises a polynucleotide sequence that encodes and is able to direct expression of a peptide of the disclosure in an individual. Suitable expression vectors are known to those of skill in the art. In various aspects, the delivery vector is a (recombinant) DNA or RNA vector known in the art, or is a plasmid comprising a polynucleotide sequence encoding a peptide of the disclosure that is operably linked to regulatory sequences conferring expression and translation of the encoded messengers. In various aspects, the vector is any DNA or RNA virus, such as, but not limited to Adenovirus, Adeno-Associated Virus (AAV), a retrovirus, a lentivirus, modified Vaccinia Ankara virus (MVA) or Fowl Pox virus, a Herpes virus, or any other viral vector capable of conferring expression of the encoded polypeptide. In various aspects, DNA vectors are non-integrating, such as episomally replicating vectors or are vectors integrating in the host genome by random integration or by homologous recombination. A delivery vector, in various aspects, comprises a liposome that comprises a nucleic acid sequence capable of directing expression of a peptide of the disclosure.

Methods

As described herein above, the disclosure provides compositions/vaccines for the treatment and/or prevention of prostate cancer. Also provided are methods of their use. Accordingly, in various embodiments, methods are provided for treating prostate cancer in a human comprising the step of administering a composition of the disclosure in an amount effective to stabilize or reduce serum PSA levels. In various aspects, the serum PSA levels are reduced by at least about 1%. In further aspects, the serum PSA levels are reduced by at least about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, about 5-fold, about 10-fold, about 100-fold or more relative to a human that was not administered the composition of the disclosure, or to a previously measured serum PSA level in the same human prior to being administered a composition of the disclosure.

In various embodiments, the disclosure provides a method of vaccinating an individual comprising the step of administering a vaccine of the disclosure to the individual.

Methods provided contemplate the use of any agent that stimulates, promotes or otherwise augments an immune response. In various embodiments, the agent is an adjuvant and/or a cytokine, and in various aspects, the cytokine is tumor necrosis factor, interleukin-2, interleukin-4, interleukin-12, interleukin-15, interleukin-17, granulocyte macrophage colony stimulating factor (GM-CSF), γ-interferons and/or combinations thereof.

In various embodiments, the peptides and GM-CSF are co-administered in a weight-to-weight ratio of at least about 1:5. Other contemplated ratios are at least about 1:6, about 1:7, about 1:8, about 1:9, about 1:10 or higher.

A peptide of the disclosure is contemplated for use in a composition as described herein in an amount effective to stabilize or reduce serum PSA levels. In various embodiments, a total of about 100 μg peptide is administered to a human. In various embodiments, a total of at least about 10 μg, about 20 μg, about 30 μg, about 40 μg, about 50 μg, about 60 μg, about 70 μg, about 80 μg, about 90 μg, about 110 μg, about 120 μg, about 130 μg, about 140 μg, about 150 μg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg, about 410 µg, about 420 µg, about 430 µg, about 440 µg, about 450 µg, about 460 µg, about 470 µg, about 480 µg, about 490 µg, about 500 µg or more is administered to a human.

In various embodiments, the peptides and GM-CSF are co-administered in multiple injections. In various aspects, the peptides and GM-CSF are co-administered in at least 2, 3, 4, 5, 6, 7, 8, 9, 10, 11, 12, 13, 14, 15, 16, 17, 18, 19, 20, 25, 30, 35, 40, 45, 50 or more injections.

Routes of administration for the PSA and/or TEM8 peptide, optionally including an agent that stimulates an immune response, include intravenous, subcutaneous, intramuscular, intraperitoneal, intradermal, oral, intranasal, intradermal, and intrapulmonary (i.e., by aerosol). The chosen route of administration will dictate the formulation that is administered and would be understood by the clinician of skill in the art.

In various embodiments, the invention provides administration of dendritic cells pulsed with said PSA and/or TEM8 peptide. In various aspects, the antigen-presenting cells are autologous to the recipient of the treatment or heterologous to the recipient of the treatment. In various aspects, the antigen-presenting cells are dendritic cells, whether autologous or heterologous, and are expanded in culture prior to being pulsed with the PSA and/or TEM8 peptide. Culture methods known in the art for expanding antigen-presenting cells are used in the practice of the invention. In various aspects, the dendritic cells are expanded in culture for at least about 8, about 9, about 10, about 11, about 12, about 13, about 14, about 15, about 16, about 17, about 18, about 19, about 20, or at least about 21 days prior to being pulsed with PSA antigen. In various aspects, the dendritic cells are pulsed with at least about 25 µg/ml, about 30 µg/ml, about 35 µg/ml, about 40 µg/ml, about 45 µg/ml, about 50 µg/ml, about 100 µg/ml, about 150 µg/ml, about 200 µg/ml, about 300 µg/ml, about 350 µg/ml, about 400 µg/ml, about 450 µg/ml or about 500 µg/ml or more.

In various embodiments, treatment of CaP with a composition or vaccine of the disclosure results in an increase in PSA peptide-tetramer staining CD8+ cells (Kim et al., J Immunology, 2000, 165: 7285-7299) of at least about 10%, at least about 20%, at least about 30%, at least about 40%, at least about 50%, at least about 60%, at least about 70%, at least about 80%, at least about 90%, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold or more. In various embodiments, treatment of CaP with a composition or vaccine of the disclosure results in an increase in TEM8 peptide-tetramer staining $CD8^+$ cells (Kim et al., J Immunology, 2000, 165: 7285-7299) of at least about 10%, at least about 20%, at least about 30%, at least about 40%, at least about 50%, at least about 60%, at least about 70%, at least about 80%, at least about 90%, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold or more.

In various embodiments, the PSA and/or TEM8 peptide(s) of the disclosure are administered with an additional agent. In various aspects, the additional agent is PROSTVAC®. In further aspects, the additional agent is GVAX. In further embodiments, methods are contemplated which include combination therapy with a chemotherapeutic agent. Chemotherapy treatment can employ anti-neoplastic agents including, for example, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Treatment Regimens

In administering any of the compositions/vaccines of the disclosure, it is contemplated that various treatment regimens are utilized.

In various embodiments, the composition/vaccine is administered in weeks 1, 4 and 10, and then every six months up to four years. Thus, the composition/vaccine is administered one or more times during weeks 1, 4 and 10 of treatment, and then the composition/vaccine is administered one or more times every six months up to four years. In some embodiments, treatment may continue beyond four years.

In various embodiments, the composition/vaccine is administered in weeks 1, 4 and 10, and then every six months up to four years, wherein an inhibitor of CTLA4 is administered in weeks 1, 4 and 10, and then every eight weeks up until week 52.

In various embodiments, the composition/vaccine is administered in weeks 1, 4 and 10, and then every six months up to four years, wherein an inhibitor of PD-1 is administered in weeks 1, 4 and 10, and then every eight weeks up until week 52.

Combinations of the above treatment regimens are also contemplated by the disclosure. For example and without limitation, administration of both an inhibitor of CTLA4 and an inhibitor of PD-1 in weeks 1, 4 and 10, and then every eight weeks up until week 52 is also contemplated. In various aspects, co-administration of a composition/vaccine of the disclosure with a TLR9 agonist is contemplated. Administration of the TLR9 agonist is contemplated in conjunction with an inhibitor of CTLA4 and/or an inhibitor of PD-1, as well as in the absence of the inhibitor of CTLA4 and/or the inhibitor of PD-1.

Administration of any of the compositions or combination of compositions of the disclosure is contemplated, in various embodiments, once a week, twice a week, three times a week, four times a week, five times a week, six times a week and seven times a week. Administration of a composition or combination of compositions of the disclosure that takes place more than once a week is contemplated to occur on either sequential or non-sequential days.

In various embodiments, administration of any of the compositions or combination of compositions of the disclosure occurs once a day, twice a day, three times a day, four times a day, five times a day or more by any one or more of the routes disclosed herein.

In various embodiments, administration of any of the compositions or combination of compositions of the disclosure occurs every week, every second week, every third week, every fourth week, every fifth week, every sixth week, every seventh week, every eighth week, every ninth week or every tenth week. Thus, administration of any of the compositions or combination of compositions of the disclosure occurs, in various embodiments, at least 1, 2, 3, 4, 5, 6, 7, 8, 9, 10, 12, 13, 14, 15, 16, 17, 18, 19, 20, 21, 22, 23, 24, 25, 26, 27, 28, 29, 30, 31 or more times per month, or every second month, or every third month, or every fourth month, or every fifth month, or every sixth month, or every seventh month, or every eighth month, or every ninth month, or every tenth month, or every eleventh month or every twelfth month or more.

Administration of any of the compositions or combination of compositions of the disclosure is contemplated, in various aspects, to occur for a duration of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more weeks. In various embodiments, administration of any of the compositions or combination of compositions of the disclosure is contemplated to occur for a duration of 1, 2, 3, 4, 5 or 6 days.

In various embodiments, any of the compositions or combination of compositions of the disclosure is contemplated to be administered to a patient for at least 1, 2, 3, 4, 5, 6, 7, 8, 9, 10 or 11 months, or at least 1, 2, 3, 4, 5, 6, 7, 8, 9, 10 or more years.

Administration of any of the compositions or combination of compositions of the disclosure is contemplated, in various aspects, to be discontinuous. In various aspects, discontinuous administration is undertaken to maximize the therapeutic efficacy of the composition or combination of compositions, or in response to one or more adverse events experienced by the patient being treated. Accordingly, administration of any of the compositions or combination of compositions of the disclosure is contemplated to occur for an amount of time and then cease for an amount of time, after which administration may resume. The amount of time that administration of a composition or combination of compositions of the disclosure is ceased is, in various embodiments, at least 1, 2, 3, 4, 5 or 6 days. In further aspects, the amount of time that administration of a composition or combination of compositions of the disclosure is ceased is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more weeks. In various embodiments, and following discontinuation of administration of any of the compositions or combination of compositions of the disclosure, it is contemplated that administration is resumed according to any of the treatment regimens disclosed herein.

Identifying a Candidate for Therapy

As exemplified below, understanding the molecular intricacies of why some patients respond to a well defined peptide target, while others do not, leads to the application of optimal vaccine strategies for appropriately selected patients and shed light on strategies to make targeted immunotherapy applicable to a wider array of patients.

The gene expression data shown in Table 1 or Table 2 provides the ability to analyze the expression profile of those patients that are strong immune responders to a therapy of the disclosure. By identifying the genes whose expression is modulated in a strong immune responder versus a non responder, it is contemplated that a further treatment regimen is aimed at either up- or down-regulating the expression of one or more gene products. By way of example, if a particular gene product is down-regulated in a strong immune responder versus a non responder, then a treatment regimen for the non responder will include an additional agent that increases expression of that gene product. In general, the disclosure contemplates modulating the gene expression profile of a non responder so that it more closely matches the gene expression profile of a strong immune responder.

Thus, in various embodiments the disclosure provides a method of administering a composition/vaccine to a patient in need thereof comprising the steps of: (i) modulating the expression of at least one gene listed in Table 1 or Table 2; and (ii) administering the composition/vaccine of the disclosure. In various aspects, the modulating increases expression and in some aspects, modulating decreases expression. It is contemplated that the modulating results in at least a 1% increase or decrease in expression of a gene. In further aspects, the modulating results in at least a 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or at least a 2-fold, 3-fold, 4-fold, 5-fold, 6-fold, 7-fold, 8-fold, 9-fold, 10-fold, 20-fold, 50-fold, 100-fold or more increase or decrease in expression of a gene.

In various aspects of the disclosure, obtaining the gene expression profile information from a patient that is in need of treatment with a composition/vaccine disclosed herein allows a clinician to determine whether that patient is likely to respond favorably to the treatment.

Thus, the disclosure provides a method of identifying a patient that is a candidate for prostate cancer therapy comprising the step of measuring expression level in a sample from a test individual of one or more genes identified in Table 1 or Table 2 relative to a reference expression level, wherein an increase or a decrease in expression of one or more of the genes identified in Table 1 or Table 2 relative to the reference expression level is determinative for identifying whether the patient is a candidate for prostate cancer therapy according to a method disclosed herein. In various aspects, the method further comprises collecting a sample from the test individual, and in another aspect the method further comprises comparing the expression level to the reference expression level.

In various aspects, a decrease in expression of a gene selected from the group consisting of tumor necrosis factor receptor superfamily-member 25 (TNFRSF-25), chemokine C—C motif receptor 7 (CCR7), and phosphoinositide-3-kinase, regulatory subunit 1 alpha (PIK3R1) and epiregulin (EREG) is indicative of the patient being a candidate for prostate cancer therapy according to a method disclosed herein.

The invention is illustrated by the following examples, which are not intended to be limiting in any way.

TABLE 2

Differentially expressed genes between immune responders and non responders.

| Gene name (symbol) | Probe set | Fold change | Affected immune-function associated pathway |
|---|---|---|---|
| 2'-5' oligoadenylate synthetase 1 (OAS1) | 202869_at<br>205552_s_at | 4.05<br>2.48 | Innate immune response |
| Vannin 1 (VNN1) | 205844_at | 2.74 | Innate immune response<br>Positive regulation of T-cell differentiation in the thymus |
| Sh2 domain containing 1B (SH2D1B) | 1553176_at | 1.92 | Natural killer cell mediated cytotoxicity |
| DEAD box polypeptide 58 (DDX58) | 218943_s_at | 1.82 | Innate immune response |
| Interferon induced transmembrane protein 3 1-8U (IFITM3) | 212203_x_at | 1.55 | Immune response |
| Mitogen-activated protein kinase 1 (MAPK1) | 1552263_at<br>1552264_a_at | 1.53 1.37 | T-cell and B-cell receptor signaling<br>VEGF signaling pathway<br>TGF-beta signaling<br>natural killer mediated cytotoxicity<br>CCR3 signaling in eosinophils<br>CXCR4 signaling pathway |
| CD58 molecule (CD58) | 216942_s_at<br>205173_x_at | 1.46<br>1.48 | IL-17 signaling pathway |
| X-ray repair complementing defective repair in Chinese hamster cells 4 (XRCC4) | 210813_s_at | 1.38 | T-cell differentiation in the thymus<br>Immunoglobulin V(D)J recombination |
| Tumor necrosis factor receptor superfamily, member 25 | 211841_s_at | 0.65 | Cytokine-cytokine receptor interaction |
| Chemokine C-C motif receptor 7 (CCR7) | 206337_at | 0.52 | Cytokine-cytokine receptor interaction |
| Phosphoinositide-3-kinase, regulatory subunit 1 alpha (PIK3R1) | 212249_at | 0.62 | T-cell activation<br>T-cell and B-cell receptor signaling<br>CXCR4 signaling pathway<br>VEGF signaling pathway<br>Toll-like receptor signaling pathway |
| Epiregulin (EREG) | 205767_at | 0.26 | positive regulation of innate immune response |

Gene expression analysis was performed on un-manipulated pre-vaccination PBMC. *Of the 166 genes differentially expressed, only genes affecting the immune function associated pathway are shown.

In various aspects, an increase in expression of a gene selected from the group consisting of 2'-5' oligoadenylate synthetase 1 (OAS1), mitogen-activated protein kinase 1 (MAPK1), Sh2 domain containing 1B (SH2D1B), vannin 1 (VNN1), CD58 molecule (CD58), DEAD box polypeptide 58 (DDX58), X-ray repair complementing defective repair in Chinese hamster cells 4 (XRCC4) and interferon-induced transmembrane protein-3 (IFITM3) is indicative of the patient being a candidate for prostate cancer therapy according to a method disclosed herein.

EXAMPLES

Example 1

Twenty eight HLA-A2+ patients with pathologically confirmed CaP who had completed vaccination with PSA146-154 peptide between July 2002 and September 2004 were included in the study [Perambakam et al., Cancer Immunology Immunotherapy 55(9): 1033-1042 (2006)]. Long-term follow-up of all patients previously enrolled in the phase IB peptide vaccine protocol was performed with the authorization of the Institutional Review Board of the University of Illinois at Chicago.

Patient Characteristics

The clinical characteristics of patients are listed in Table 3, below. All patients had undergone radio-therapy or surgical ablation of the prostate a minimum of 6 weeks prior to initiation of vaccine study. Patients either had advanced local disease with high risk of recurrence based on the presence of T3, T4 disease, a serum PSA level ≥10 ng/ml or a Gleason grade ≥7 (Group A), or they had confirmed metastatic disease which was associated with declining serum PSA on ADT or a stable or improving bone scan or CT scan in response to hormone therapy (Group B). All patients were immunologically reactive to a panel of mumps, measles, and candida.

The Unique Patient Identifying Number (UPIN) assigned in the original report was retained. Relevant information pertinent to morbidity, disease specific mortality and OS was collected from patients and/or family members following appropriate informed consent.

TABLE 3

Patient baseline characteristics.

| Characteristic | Group A | Group B | Protocol-1 | Protocol-2 | Total |
|---|---|---|---|---|---|
| | n = 14 | n = 14 | n = 14 | n = 14 | n = 28 |
| Age | | | | | |
| median (average) | 61.5 (62.2) | 62 (64) | 64.5 (65.2) | 60.5 (61) | 62 |
| range | 51-73 | 51-80 | 51-80 | 51-75 | 51-80 |
| Race | | | | | |
| white | 10 | 13 | 12 | 11 | 23 |
| black | 2 | 1 | 1 | 2 | 3 |
| other | 2 | 0 | 1 | 1 | 2 |
| ECOG PS | | | | | |
| 0 or 1 | 14 | 14 | 14 | 14 | 28 |
| 2 or 3 | 0 | 0 | 0 | 0 | 0 |
| Disease status | | | | | |
| undetectable (PSA 0) | 3 | 4 | 5 | 2 | 7 |
| measurable | 0 | 7 | 2 | 5 | 7 |
| increased PSA only | 11 | 3 | 7 | 7 | 14 |
| Sites of Disease | | | | | |
| bone | 0 | 4 | 2 | 2 | 4 |
| soft tissue | 0 | 4 | 0 | 4 | 4 |
| Family History | | | | | |
| positive | 4 | 3 | 5 | 2 | 8 |
| negative | 9 | 9 | 6 | 12 | 17 |
| unknown | 1 | 1 | 2 | 0 | 3 |
| Gleason Score | | | | | |
| median (average) | 7 (7.14) | 7 (7.3) | 7 (7.2) | 7.5 (7.25) | 7 |
| range | 4-9 | 5-10 | 5-10 | 4-9 | 4-10 |
| PSA at diagnosis | | | | | |
| median (average) | 5.8 (9.1) | 15.25 (28.4) | 8.4 (12.3) | 13.4 (24.3) | 10.5 |
| range | 4-23.4 | 3.4-139 | <4-23.4 | 3.4-139 | 3.4-139 |
| PSA at study entry | | | | | |
| median (average) | 0.32 (3.66) | 0.4 (2.6) | 0.4 (2.75) | 0.4 (3.5) | 0.4 |
| range | 0-12.5 | 0-13.8 | 0-12.1 | 0-13.8 | 0-13.8 |
| Local Therapy | | | | | |
| Radical Prostatectomy (RPE) | 2 | 4 | 2 | 4 | 6 |
| RPE + (External Beam Radiation Therapy) EBRT | 7 | 4 | 8 | 3 | 11 |
| EBRT, primary | 2 | 4 | 2 | 4 | 6 |
| other | 3 | 2 | 2 | 3 | 5 |
| Hormone Rx | | | | | |
| none | 10 | 0 | 5 | 5 | 10 |
| first line | 4 | 11 | 8 | 7 | 15 |
| second line | 0 | 2 | 1 | 1 | 2 |
| ≥3 therapies | 0 | 1 | 0 | 1 | 1 |
| Basal biochemistry | | | | | |
| Alkaline Phosphatase | 48-90 | 49-105 | 49-90 | 50-105 | 48-105 |
| Haemoglobin | 12.8-16.6 | 11.5-16.9 | 11.5-15.7 | 12.2-16.9 | 11.5-16.9 |
| Creatinine | 0.7-1.3 | 0.8-1.2 | 0.8-1.3 | 0.7-1.3 | 0.7-1.3 |

All patients had completed primary therapy a minimum of 6 weeks prior to enrollment in the vaccine study.

Vaccine Protocol and Dendritic Cell Culture

Patients were either treated by intradermal administration of PSA146-154 peptide and GM-CSF (protocol 1, n=14) or by intravenous administration of peptide-pulsed, autologous dendritic cells (DC) (protocol 2, n=14) as previously detailed [Perambakam et al., Cancer Immunology Immunotherapy 55(9): 1033-1042 (2006)]. Patients were vaccinated on three occasions (week 1, 4 and 10) and monitored. DC was derived from monocyte and cultured in serum free AIM-V (Life Technologies, Grand Island, N.Y.) medium with IL-4 and GM-CSF for a total of 8 days in T-150 flasks in clinical grade sterile laminar airflow hood per the method of Lau et al [Lau et al., Journal of Immunotherapy 24: 66-78 (2001)]. Release criteria for the final DC product included sterile bacterial, fungal and mycoplasmia cultures, negative endotoxin per *Limulus* Amoebacyte lysate assay, viability of at least 90% and greater than 50% CD86, CD80, HLA-DR or CD1a positive cells and less than 10% CD 14 positive cells by flow cytometric analysis. The final DC product was divided into 3 equal parts. The first infusion included fresh DC while the 2nd and 3rd infusions consisted of frozen DC product. At the time of infusion, DC were rapidly thawed at 37° C., again checked for sterility and viability and administered intravenously to patients.

Results—Dendritic Cell Product

Two healthy donors and 14 patients underwent 7-9 liter leukapheresis and DC were cultured for 8 days under identical conditions and phenotyped. The average HLA-DR % was 54.51 (median 52.92), the average CD86% was 58.77 (median 62.56), the average CD1a % was 28.17 (median 30.95) and the average CD14% was 1.31 (median 0 or negative expression). DC product was also phenotyped for CD80 and CD83. However, only 2 of 14 patients DC showed CD80 expression, while CD83 was negative in all the patients. The average percent HLA-DR, CD86, CD1a and CD14 were 70.03%, 76.6%, 30.58% and 5.94%, respectively in healthy individuals. The yield of total DC from PBMC ranged from 0.94 to $2.02 \times 10^8$ cells (average 1.499, median 1.555) per vaccine in the 14 patients. Functional activity of DC product also was tested in several patients. DC, cultured in IL-4/GM-CSF for 8 days were able to stimulate significant (>20-fold) allogeneic T-cell proliferative responses compared to DC pulsed autologous T-cells. Additionally, upon maturation with TNF-α or LPS for 24 hours, the expression of CD83, a late DC marker, was up-regulated (negative expression to 25% expression).

Delayed Type Hypersensitivity Skin Testing

Immune responses were monitored by Delayed Type Hypersensitivity (DTH) skin testing on weeks 4, 14, 26, ad 52 by intradermal injection of 0 (carrier only), 1, 10 and 20 microgram of peptide dissolved in 200 microliter of 33% DMSO as previously detailed [Perambakam et al., Cancer Immunology Immunotherapy 55(9): 1033-1042 (2006)]. DTH reactions were measured at 48-72 hours following injection. An induration of ≥15 mm was considered as a positive reaction.

T-Cell Culture and Peptide-Specific Stimulation of Peripheral Blood Mononuclear Cells Frozen PBMC obtained at various study time points, pre-vaccine (1 to 3 weeks prior to vaccination), week 26 and week 52 were rapidly thawed, washed, checked for viability and re-suspended in RPMI-1640 medium (BioWhittaker, Walkersville, Md.) containing 10% human AB serum (complete medium). Viability was >90% (range 90 to 99%, mean 95±1.26). PBMC ($2 \times 10^6$) were plated in 24 well plates (Nunc, Naperville, Ill.) and cultured in complete medium containing PSA146-154 peptide (SEQ ID NO: 3) (20 ug/ml) and IL-2 (20 U/ml) for 7±1 days (1 cycle). PBMC were alternatively stimulated with HLA-A2 binding control peptide, Flu-M1, in some patients. Spent medium was aspirated and replenished with complete medium plus IL-2 and re-stimulated with irradiated autologous PBMC pulsed with peptide for 2 additional cycles prior to tetramer and cytokine analysis.

Tetramer Analysis

PSA146-154 peptide stimulated PBMC ($1 \times 10^6$ per tube) were doubly stained with PSA 146-154 peptide-tetramer-PE (Immunomics, San Diego, Calif.) and CD8-FITC (BD Biosciences, San Diego, Calif.) at room temperature for 30 minutes in phosphate-buffered saline containing 0.5% para-formaldehyde (Sigma, St. Louis, Mo.). Cells were washed, re-suspended in buffer and analyzed by a Calibur flow cytometer (Becton Dickinson, Mountain View, Calif.). Cells also were stained separately with a negative control tetramer-PE, of unknown sequence that does not recognize CD8+ T-cells of any HLA alleletype, to assess the level of background PE fluorescence. As a positive control, tetramer-PE staining for Flu-M1 peptide also was performed in some of the patients. The percentage of CD8+ tetramer+ double positive cells was determined from the quadrant dot plots per Cell Quest software (Becton Dickinson, Mountain View, Calif.). The results were represented as the number of tetramer+ cells per CD8+ cells and are calculated as the number of tetramer+CD8+ cells divided by total number of CD8+ cells.

Results—Immunological Responses

Three distinct read-outs were used to detect specific immune responses. First via the induction of DTH skin responses to PSA146-154 peptide in vivo, second via detection of CD8+ PSA146-154 peptide-tetramer+ T-cells, and third via PSA146-154 peptide induced release of IFN-γ in pre-versus post-vaccine PBMC samples. In vitro sensitization of PBMC with PSA146-154 peptide was essential prior to tetramer and CBA analysis to detect specific T-cells in peripheral blood. This procedure was applied uniformly to all specimens and was necessary to overcome high background. Similar techniques have been employed in previous cancer vaccine trials [Lau et al., Journal of Immunotherapy 24: 66-78 (2001); Meidenbauer et al., Prostate 43: 88-100 (2000)]. Lau et al. have shown induction of peptide-specific CTL stimulated twice with melanoma-associated peptides over 24 days in IFN-γ ELISA [Lau et al., Journal of Immunotherapy 24: 66-78 (2001)]. Meidenbauer et al. have shown PSA-reactive responses per IFN-γ ELISPOT following two stimulations in patients with prostate cancer [Meidenbauer et al., Prostate 43: 88-100 (2000)].

et al. Tetramer assay denotes a physical measure of the number of CD8+ PSA 146-154 peptide-specific T-cells while the specific release of IFN-γ cytokine following the recognition T2 pulsed targets cells represents a functional readout of T-cells. Although, IFN-γ was the predominant cytokine expressed, specific release of TNF-α, IL-4 and IL-5 was also observed (Table 4, below).

TABLE 4

Induction of specific cytokine responses.

| | Specific cytokine levels post vaccination[1] (pg/ml) | | | | | | | |
|---|---|---|---|---|---|---|---|---|
| | IFN-γ | | TNF-α | | IL-4 | | IL-5 | |
| Patient code | wk 26 | wk 52 | wk 26 | wk 52 | wk 26 | wk 52 | wk 26 | wk 52 |
| UPIN13 | 141.4 | 0 | 43.5 | 3.8 | 0 | 0 | 824.4 | 25.5 |
| UPIN16 | 44.4 | 241.6 | 0 | 100.2 | 38.4 | 53.6 | 0 | 532.9 |
| UPIN28 | 525.4 | 847.9 | 33.2 | 134.6 | 86.1 | 80.9 | 989.8 | 373.7 |
| UPIN50 | −20.7 | −20.7 | 0 | 0 | 0 | 0 | 0 | 0 |
| UPIN55 | 262.7 | 66 | 12.3 | 2.5 | 18.7 | 9.6 | 77.4 | 37.8 |
| UPIN40 | 313.5 | 488.9 | 31.5 | 39.9 | 34 | 0 | 320.9 | 0 |
| UPIN45 | 30.6 | 88.8 | 25.8 | 3 | 2.5 | 7.2 | 0 | 8.3 |
| UPIN71 | 20.9 | 31 | 0 | 0 | 0 | 0 | 0 | 0 |
| UPIN43 | −3.5 | −11.2 | 0 | −0.5 | 1.1 | 0 | −0.2 | −0.2 |
| UPIN2 | 63.9 | −50.2 | 10.7 | 0 | 9.3 | 13.1 | 21.8 | 0 |
| UPIN21 | 1064.5 | −9.3 | 18.7 | 0 | 30.4 | 0 | 92 | 0 |
| UPIN27 | 2236 | ND | 37 | ND | 13.8 | ND | 1.5 | ND |
| UPIN38 | 112.1 | 1.3 | 2.8 | 0 | 11.5 | 0 | 18.9 | 0 |
| UPIN82 | −3.2 | −3.2 | −0.2 | −0.2 | 0 | 0 | −2.4 | −2.4 |
| UPIN49 | 0 | 113.5 | 0 | 113.5 | 0 | 79.9 | 0 | 0 |
| UPIN69 | 1293.5 | 133.4 | 26.7 | 0 | 20.4 | 0 | 46.7 | 0.1 |
| UPIN88 | −34.5 | 230.4 | 0 | 4.6 | 0 | 2.4 | −2.9 | 0.8 |
| UPIN53 | 25.3 | 2417.4 | 0 | 0.3 | 0.3 | 94.3 | −1.2 | 29.8 |
| UPIN81 | −2.9 | −2.9 | 0 | 0 | 0 | 0 | 0 | 0 |
| UPIN51 | 0 | 0 | 0 | 0 | 0 | 0 | 0 | 0.2 |
| UPIN26 | 255.5 | 1211.4 | −0.3 | 69.4 | 10 | 201 | 2 | 875.2 |
| UPIN32 | 0 | 0 | 0 | 0 | 0 | 0 | 0 | 0.7 |
| UPIN35 | −10.4 | 24.3 | 0 | 0.3 | −12.4 | −8.5 | 0 | 46.4 |
| UPIN37 | 1.4 | 0 | 0 | 0 | 0 | 0 | 0 | 0 |
| UPIN85 | 0 | 0 | 0 | 0.7 | 0 | 0 | 0 | 0 |
| UPIN89 | −46.9 | −46.9 | −1.2 | −1.2 | −13 | −12.7 | −16.8 | −16.8 |
| UPIN67 | 40.3 | 0 | 0 | 0 | 0 | 0 | −3.5 | −2.6 |
| UPIN70 | 130.9 | 0 | −0.6 | −0.6 | −4.7 | −4.7 | −0.6 | −2.1 |

[1]Cytokine responses were evaluated on PBMC at pre-vaccine, week 26 and 52 as detailed in methods section. Value represents absolute changes in post-vaccine cytokine levels minus the pre-vaccine levels are shown. ND denotes not done.

Overall, fifty percent of patients demonstrated positive DTH skin responses to PSA146-154 peptide (Table 5, below). Baseline (week 4) DTH responses were negative in a majority of patients (13 of 14 patients), however, measurable induration became evident over time and increased with successive DTH testing. Responses were dose-dependent with increasing doses of the PSA146-154 peptide eliciting increasing degrees of induration in responding patients [Perambakam et al., Cancer Immunology Immunotherapy 55(9): 1033-1042 (2006)]. Injection of carrier only, i.e. 33% DMSO did not cause significant induration. Both CD4+ and CD8+ T-cells were derived from the positive DTH skin biopsy that demonstrated specific cytolytic and cytokine activity as detailed in a previous publication [Perambakam et al., Cancer Immunology Immunotherapy 55(9): 1033-1042 (2006)].

Fourteen of 28 patients developed ≥4-fold increase in CD8+ PSA146-154-tetramer+ T-cells at week 26 and/or week 52 over baseline levels (Table 5). On average, 3.5 CD8+ PSA146-154-tetramer+ T-cells was observed for every 100 CD8+ T-cells at week 26, while an average of 2.0 CD8+ PSA146-154-tetramer+ T-cells were detected for every 100 CD8+ T-cells at week 52. On an average, 1.0 CD8+ PSA146-154-tetramer+T-cell could be detected per 100 CD8+ T-cells prior to the onset of immunotherapy. FIG. 1 is a representative tetramer staining analysis showing increased CD8+ PSA146-154-tetramer+ T-cells post vaccine (week 26) compared to pre-vaccine following in vitro sensitization of PBMC with PSA146-154 peptide. Tetramer responses were not detectable in un-stimulated PBMC population. Comparable results were observed by Lau and co-workers in a peptide-DC based melanoma study [Lau et al., Journal of Immunotherapy 24: 66-78 (2001)].

Similarly, 14 of 28 patients demonstrated specific release of IFN-γ (defined as ≥100 ng/ml of absolute change) by week 52 from the outset of immunotherapy. Specific release of other cytokines, namely, TNF-α, IL-4 and IL-5 also was observed (Table 4). The CBA analysis in the current study was performed with unsorted T-cell populations, therefore it was not possible to determine whether IFN-γ was released by CD8+ and/or CD4+ T-cells.

Eight of 14 (57%) positive tetramer responders also mounted specific DTH responses to PSA146-154 peptide, while only 4/14 (28%) tetramer non-responders were positive for DTH responses to the peptide, indicating concordance between the development of peptide-specific DTH responses in the skin and specific T-cell immune responses in peripheral blood of patients.

TABLE 5

Immunological outcomes based on specific DTH, tetramer and IFN-γ responses.

| Patient Code | DTH responders positive (+) negative (−) | Fold increase in tetramer | | Tetramer responders positive (+) negative (−) | Absolute change in IFN-γ | | IFN-γ responder positive (+) negative (−) |
|---|---|---|---|---|---|---|---|
| | | week 26 | week 52 | | week 26 | week 52 | |
| UPIN13 | + | 22.25 | 34.49 | + | 141.4 | 0 | + |
| UPIN16 | + | 22.77 | 121.29 | + | 44.4 | 241.6 | + |
| UPIN28 | + | 29.25 | 12.5 | + | 525.4 | 847.9 | + |
| UPIN40 | + | 15.85 | 2.47 | + | 313. | 488.9 | + |
| UPIN45 | + | 11.39 | 6.97 | + | 30.6 | 88.8 | − |
| UPIN49 | + | 1.75 | 1.71 | − | 0 | 113.5 | + |
| UPIN50 | + | 6.11 | 3.8 | + | −20.7 | −20.7 | − |
| UPIN51 | + | 0.69 | 0.26 | − | 0 | 0 | − |
| UPIN53 | + | 1.58 | 0.69 | − | 25.3 | 2417.4 | + |
| UPIN55 | + | 2.71 | 5.28 | + | 262.7 | 66 | − |
| UPIN69 | + | 2.09 | 0.23 | − | 1293.5 | 133.4 | + |
| UPIN71 | + | 4.91 | 4.82 | + | 20.9 | 31 | − |
| UPIN81 | + | 1.72 | 0.09 | − | −2.9 | −2.9 | − |
| UPIN88 | + | 1.42 | 0.06 | − | −34.5 | 230.4 | + |
| UPIN2 | − | 3.09 | 5.83 | + | 63.9 | −50.2 | − |
| UPIN21 | − | 0.51 | 5.43 | + | 1064 | −9.3 | + |
| UPIN26 | − | 0.35 | 0.81 | − | 255.5 | 1211.4 | + |
| UPIN27 | − | 82.11 | ND | + | 2236 | ND | + |
| UPIN32 | − | 1.13 | 1.05 | − | 0 | 0 | − |
| UPIN35 | − | 1.31 | 0.09 | − | −10.4 | 24.3 | + |

TABLE 5-continued

Immunological outcomes based on specific DTH, tetramer and IFN-γ responses.

| Patient Code | DTH responders positive (+) negative (−) | Fold increase in tetramer | | Tetramer responders positive (+) negative (−) | Absolute change in IFN-γ | | IFN-γ responder positive (+) negative (−) |
|---|---|---|---|---|---|---|---|
| | | week 26 | week 52 | | week 26 | week 52 | |
| UPIN37 | − | 0.80 | 0.26 | − | 1.4 | 0 | − |
| UPIN38 | − | 10.79 | 1.37 | + | 112.1 | 1.3 | + |
| UPIN43 | − | 1.11 | 5.06 | + | −3.5 | −11.2 | − |
| UPIN67 | − | 1.72 | 0.07 | − | 40.3 | 0 | − |
| UPIN70 | − | 0.46 | 1.85 | − | 130.9 | 0 | + |
| UPIN82 | − | 4.47 | 0.24 | + | −3.2 | −3.2 | − |
| UPIN85 | − | 2.50 | 0.08 | − | 0 | 0 | − |
| UPIN89 | − | 2.93 | 0.02 | − | −46.9 | −46.9 | − |

Fourteen of 28 (50%) patients developed positive tetramer, IFN-γ and/or DTH responses to PSA146-154 peptide by week 52. A positive tetramer response is defined as ≥4-fold increase in tetramer levels by week 52 over pre-vaccine levels, while positive IFN-γ response was defined as ≥100 ng/ml of absolute change in cytokine levels at week 26 or 52 minus pre-vaccine levels. A positive DTH reaction is defined as ≥15 mm of induration to PSA146-154 peptide. A stringent cut-off value was taken into consideration to measure true immune responses and to avoid false positives.

Figure 2:
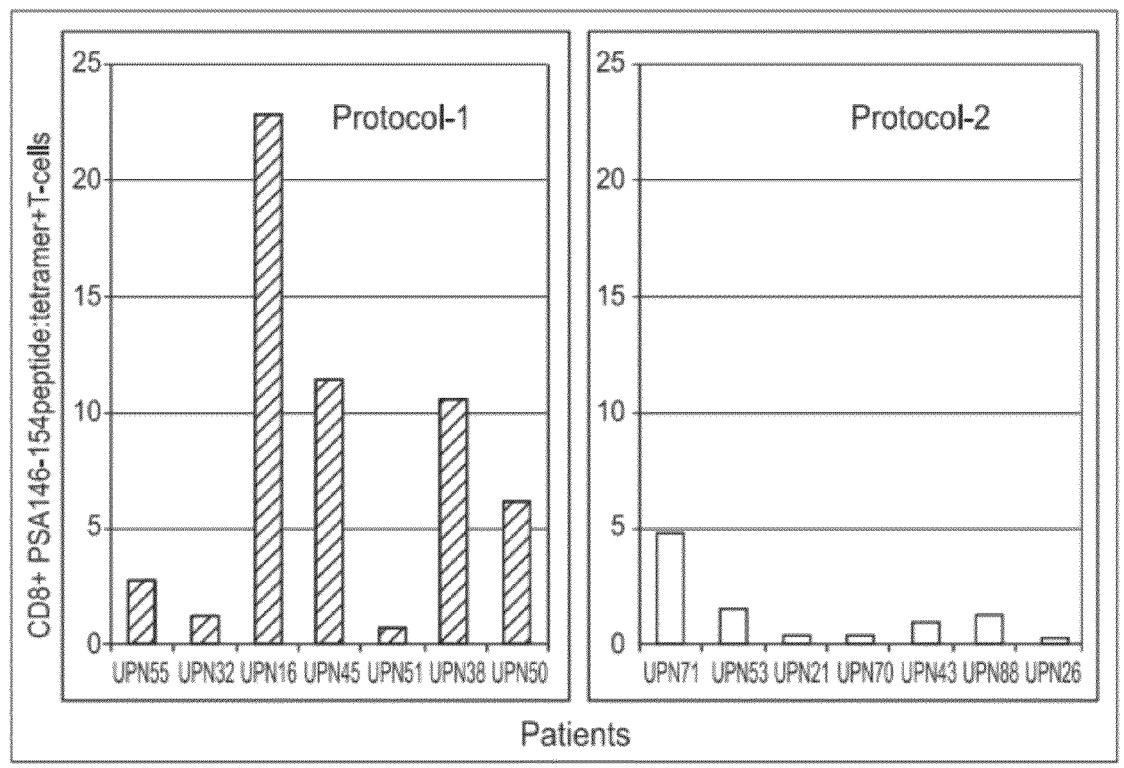
FIG. 2 depicts a comparison of tetramer levels based on vaccination methods. The average fold increase in CD8+ PSA146-154peptide:tetramer+ T-cells at week 26 over pre-vaccine levels was 4.4 greater on protocol-1 (PSA146-154 peptide admixed with GM-CSF injected intradermally) as compared to protocol-2 (intravenous administration of peptide-pulsed, autologous DC) particularly in high-risk patients with locally advanced disease (p-value=0.007).

The method of vaccination appeared to impact tetramer response. The average fold increase in CD8+ PSA146-154 peptide:tetramer+T-cells in patients vaccinated under protocol-1 (intradermal peptide) was 4.4 times higher than achieved with protocol-2 (peptide pulsed DC) in high-risk patients with locally advanced disease at 6 months following vaccination (p-value=0.007) (FIG. 2). However, no significant differences remained at week 52, possibly due to declining tetramer responses over time.

Cytokine Bead Array Analysis

PSA146-154 peptide stimulated PBMC also were evaluated for specific release of cytokines following recognition of peptide-pulsed targets. Cytokines released into the culture supernatant, including, IFN-γ, TNF-α, IL-4, IL-5 and IL-10, were measured concurrently by cytokine bead array analysis (BD Biosciences, San Diego, Calif.) as described earlier [Perambakam et al., Cancer Immunology Immunotherapy 55(9): 1033-1042 (2006)]. Briefly, the antigen presenting cell line, T2 (ATCC, Manassas Va.), was used as a stimulator and was pulsed with 20 μg/ml of PSA-peptide or control HLA-A2 binding peptide, HIV-RT476-484 or diluent alone (0.4% volume by volume). T2 cells (25,000/well) were cultured with T-cells (100,000/well) in complete medium containing 30 U/ml of IL-2 in a total volume of 1 ml per well in 48-well plates. This particular stimulator to responder ratio was found to be optimal for culture in 48-well plates. Cells were incubated at 37° C. for 24 hours in 5% $CO_2$ atmosphere. Supernatants were harvested and stored in sterile vials at −80° C. At the time of assay, samples were thawed and cytokines were measured using a CBA kit as per the manufacturer's protocol with a Calibure flow cytometer (Becton Dickinson, Mountain View, Calif.). Results were represented as net cytokine levels (pg/ml) which were obtained by subtracting non-specific background responses (T2 cells pulsed with HIV-RT476-484 or diluent).

Microarray and Bioinformatic Analysis

Total RNA was extracted from pre-vaccine PBMC samples of patients with both strong specific DTH and tetramer responses (UPIN13, UPIN28, UPIN40, UPIN45 and UPIN71) and patients with negative DTH and tetramer responses (UPIN32, UPIN35, UPIN37 and UPIN70) using RNeasy mini kit (Qiagen, Valencia, Calif.). The quantity and quality of RNA were estimated with a Nanoprop™ 3300 Fluorospectrometer (Thermo Fisher Scientific, Waltham, Mass.), and an Agilent bioanalyzer, respectively (Agilent Technologies, Santa Clara, Calif.). All RNA samples were stored at −80° C. Microarray analysis was performed at the functional Genomics Laboratory of the University of Illinois at Urbana Champaign, using the human genome U133 plus 2.0 chips (Affymetrix, Santa Clara, Calif.). Data was extracted from the Affymetrix array and normalized by the Robust Multichip Average (RMA) method [Irizarry et al., Nucleic Acids Research 31(e15) (2003)]. Class comparison analysis was conducted per the Biometric Research Branch (BRB) array tool (National Cancer Institute, Bethesda, Md.). Gene expression data was compared between strong immune responders (UPIN13, UPIN28, UPIN40, UPIN45 and UPIN71-positive DTH and tetramer responses) and non responders (UPIN32, UPIN35, UPIN37 and UPIN70-negative DTH and tetramer responses).

Results—Gene Expression Profiles of Immune Responders Versus Non Responders

Affymetrix human genome U133 plus 2.0 chips array analysis was performed on pre-vaccine PBMC, in order to identify genes and gene pathways that are differentially expressed between patients who developed strong immune responses versus patients who did not. Immune responders included patients with strong tetramer (>4.9 fold) responses in conjunction with a positive DTH skin reaction to the PSA146-154 peptide, while non-responders included patients who were negative for both tetramer and DTH responses.

Class comparison analysis per BRB array tools revealed that 166 of 54,675 genes were differentially expressed at a significance level of p<0.005 (Table 1). Predictably, the gene ontology class belonging to the biological process category of immune system development (GO ID: 0002520) was affected with an observed to expected ratio of 2.1. Of the 166 differentially expressed genes, 12 genes were involved in the immune function associated pathway (Table 2). A 4-fold increase in 2'-5' oligoadenylate synthetase 1 (OAS1) was noted in immune responders versus non-responders. Other genes that were over-expressed included, mitogen-activated protein kinase 1, Sh2 domain containing 1B, vannin 1, CD58 molecule and interferon-induced transmembrane protein-3. Tumor necrosis factor receptor superfamily-member 25, chemokine C—C motif receptor 7 and phosphoinositide-3- kinase, regulatory subunit 1 alpha genes and epiregulin showed decreased expression in immune responders versus non-responders.

Clinical Evaluation

The disease status of patients was monitored by clinical examination and serial serum PSA levels scans on weeks 1, 4, 7, 14, 26, and 52. Biochemical progression (P) was defined as at least a 20% increase in serum PSA at week 52 over week 1 (study entry) with an absolute PSA value >0.2 ng/ml. Stable biochemical disease or non progression (NP) was defined as less than a 20% increase in serum PSA over week 1 with an absolute PSA value less than 0.2 ng/ml.

Survival status was established for all 28 vaccinated patients by review of the Social Security Death Registry Index and by direct contact of patients or their relatives. Time (in months) from the onset of vaccine therapy (week 1) till death or until May 1, 2010 for patients who were deceased or surviving, respectively was calculated followed by computation of OS per Kaplan-Meier analysis (SAS software version 9.2, Cary, N.C.). The median follow-up period was 6.30 years (mean 5.36 years; range 1.35 to 7.68 years).

Results—Clinical Outcomes: Toxicity, Serum PSA and Survival Status

Toxicity: Both methods of vaccination were well tolerated with no treatment related grade 3/4 toxicities, graded according to the NIH Common Terminology Criteria for Adverse Events, version 3.0. Mild pain, itching, and erythema with or without induration were observed at the site of injection for all patients treated under protocol-1. There were no late safety concerns or deleterious sequelae identified after six to eight years of monitoring.

PSA progression: Thirteen of 27 (48.1%) patients manifested stable or declining serum PSA, while 14 of 27 (51.6%) patients evidenced PSA progression at one year following the onset of PSA146-154 peptide vaccine therapy. One patient, UPIN27, did not return for follow-up at week 52 and hence, his biochemical status was not evaluable. However, the survival status was determinable in all 28 patients. As of May 1, 2010, 15 of 28 (54%) patients were alive while 13 (46%) patients had died. In most patients, death was CaP specific, however, one patient, UPIN16, died of late occurring esophageal cancer.

Figure 3:
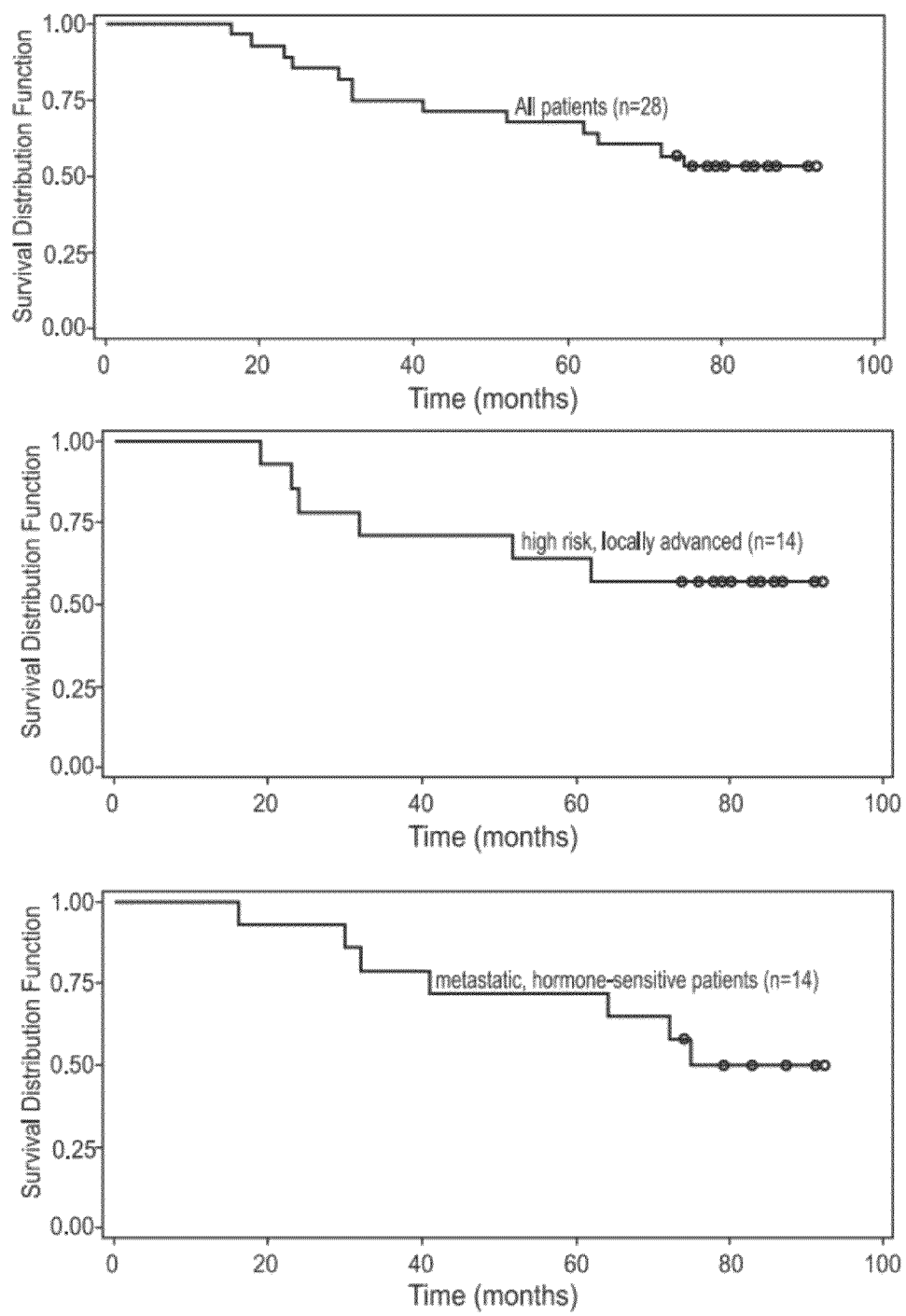
FIG. 3 depicts overall survival for high risk, locally advanced and metastatic hormone-sensitive CaP. The mean OS was 60 months (95% CI 51 to 68 months) for all patients (upper panel). The median OS was greater than 84 months for patients with high risk, locally advanced disease (middle panel), while the median OS was 75 months for patients with metastatic, hormone-sensitive CaP (lower panel) at a median follow-up of 6.30 years since the onset of immunotherapy.

Survival: OS is the most definitive standard to assess the outcome of anticancer therapies and was determined per Kaplan-Meier analysis eight years after the initiation of the protocol. The median follow-up period for individual patients was 6.30 years (range 1.35 to 7.68 years) from the onset of immunotherapy. The mean OS was 60 months (95% CI 51 to 68 months) for all patients (FIG. 3—upper panel). The median OS has not yet been reached for patients with high risk, locally advanced disease, exceeding 84 months. On the other hand, the median OS was 75 months for patients with metastatic, hormone-sensitive CaP (FIG. 3—middle and lower panel).

Correlation of Clinical Outcome with the Induction of Specific Immune Responses

Figure 4:
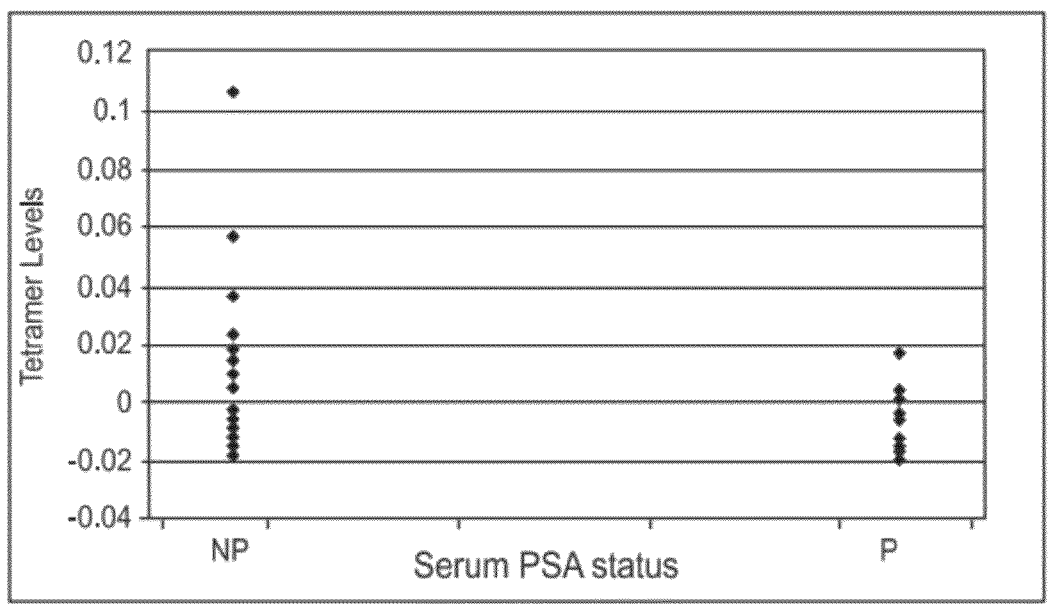
FIG. 4 depicts the correlation between augmented specific tetramer responses and serum PSA status. The average tetramer measurements at week 26 minus pre-vaccine levels (A26) inversely correlated with lower risk of serum PSA progression at six months following the onset of immunotherapy (p=0.02). "NP" denotes stable biochemical disease or non progression, while "P" denotes biochemical progression.

The development of specific T-cell immune responses was correlated with patients' serum PSA and survival status. The results indicate that the average tetramer measurements at week 26 minus pre-vaccine levels inversely correlated with changes in serum PSA levels (FIG. 4, p=0.02). Thus, a decreased risk of biochemical progression was observed in patients who developed augmented tetramer responses at six months compared to pre-vaccination levels. No significant correlation remained at one year, as specific immune responses became attenuated over time.

Figure 5:
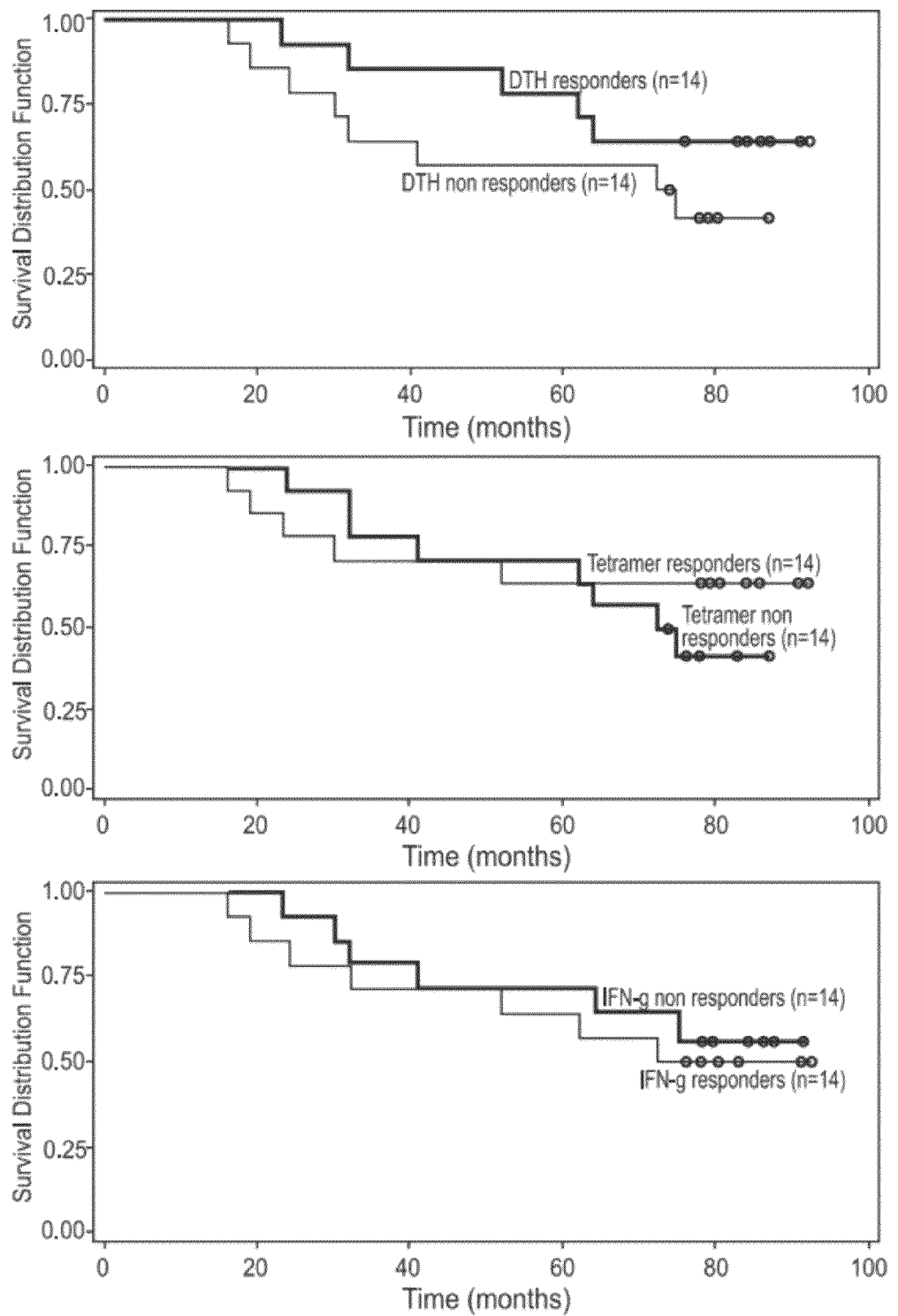
FIG. 5 depicts a comparison of overall survival between immune responders versus non responders. There was a trend towards greater OS in men with high-risk, hormone-sensitive CaP who developed strong specific DTH or tetramer response (upper and middle panel, respectively) following vaccination with PSA146-154 peptide.

OS of patients who developed positive DTH responses, tetramer or IFN-γ responses to PSA146-154 peptide versus patients who did not develop specific immune responses were correlated by log-rank testing. The mean OS was 58 months (95% CI, 50 to 66 months) for strong DTH responders versus 54 months (95% CI, 41 to 68 months) for non-responders (p=0.21). The mean OS was 61 months (95% CI, 50 to 71 months) in patients who showed strong tetramer responses versus 44 months (95% CI, 35 to 52 months) for non-responders (p=0.46). The mean OS was 61 months (95% CI, 50 to 73 months) in patients who showed strong IFN-γ responses versus 55 months (95% CI, 43 to 68 months) for non-responders (p=0.65). Although these findings did not reach statistical significance, the patients who developed strong T-cell immunity in terms of specific DTH and tetramer responses to PSA146-154 peptide within one year following vaccination, demonstrated a trend towards greater OS (FIG. 5).

Statistical Analysis

A marginal longitudinal model was used to compare tetramer or cytokine measurements over time within similar groups of patients. The dependent variable was the log of the tetramer values or cytokine measurements. The independent variables included intercept, group, time dummies, and interactions between group and time dummies. Pearson correlation coefficients were used to evaluate correlation between the fold increase in tetramer levels and absolute change IFN-γ cytokine. Spearman analysis was used to evaluate the correlation of tetramer or cytokines values with serum PSA status. The two sample t-test with unequal variance was used to identify genes that were differentially expressed between immune responders and non responders per BRB array tools. OS was evaluated per Kaplan-Meier analysis. The log-rank tests were used to evaluate differences in survival curves.

Conclusions

In the current study, 15 of 28 (54%) patients were alive at eight years from the initiation of the protocol while 13 (46%) patients had died. Of note, a trend towards greater survival in men with high-risk, hormone-sensitive CaP who developed strong specific DTH or tetramer responses following vaccination with PSA146-154 peptide was observed. Two previous cancer vaccine studies conducted in hormone-refractory CaP patients showed that survival positively correlated with the induction of specific immune responses [Thomas-Kaskel et al., International Journal of Cancer 119(10): 2428-2434 (2006); Gulley et al., Cancer Immunology Immunotherapy 59(5): 663-674 (2010)]. The demonstration of statistically significant survival advantages by immunization of hormone-sensitive CaP patients with longer life expectancies will require extended periods of observation and expanded patient cohorts. Importantly, the availability of quantitative metrics for monitoring the induction of specific T-cell immunity to defined target antigens as in the study presented herein, should provide an important surrogate for gauging vaccine efficacy, if a causal relationship between the induction of specific T cell immunity and survival advantages can be definitively established. This in turn would speed vaccine optimization for early phases of CaP.

DC are central to successful vaccination and can be directly targeted in vivo with antigen and adjuvants, such as GM-CSF, as demonstrated in early pioneering studies [Palucka et al., Immunological Reviews 220: 129-150 (2007); Disis et al., Blood 88(1): 202-210 (1996); Disis et al., Journal of Clinical Oncology 20(11): 2624-2632 (2002)]. Alternatively, ex vivo generated monocytic or CD34-derived DC loaded with tumor antigen can be utilized for specific active immunotherapy of cancer patients [Nestle et al., Nature Medicine 4(3): 328-332 (1998); Thurner et al., Journal of Experimental Medicine 190(11): 1669-1678 (1999); Banchereau et al., Cancer Research 61(17): 6451-6458 (2001); Timmerman et al., Blood 99(5): 1517-1526 (2002)]. However, DC-based vaccine formulations involve laborious manipulations ex vivo and incur considerable cost. Therefore, the efficacy of PSA146-154 peptide vaccine by both techniques was compared in a randomized fashion. The results revealed that the average fold increase in CD8+ PSA146-154peptide:tetramer+ T-cells was 4.4 times higher in patients vaccinated with PSA146-154 peptide admixed with GM-CSF injected intradermally as compared to intravenous administration of peptide-pulsed, autologous DC. The finding that a simple method of intradermal vaccination is efficacious has important implications for the affordability and applicability of the technique to the general population. These results are corroborated by a similar study, wherein, intradermal injection of E75 HER2/neu peptide GM-CSF was found to be efficacious in high risk node positive breast cancer patients [Peoples et al., Journal of Clinical Oncology 23(30): 7536-7645 (2005)].

The study presented herein showed that a set of molecular determinants expressed within PBMC distinguish immune responders and non responders undergoing vaccination with a peptide-based cancer vaccine. Genomic and bioinformatics analysis revealed 166 genes that are differentially expressed between strong immune responders versus non responders. In particular, genes associated with innate immune response were over-expressed, including, OAS1, which belongs to a family of IFN-stimulated proteins [Haralambieva et al., Human Immunology 71(4): 383-391 (2010)]. Interestingly, OAS1 also is postulated to be associated with radiation resistance in human breast cancer and CaP cell lines and with the regulation of cell growth in mammary and prostate glands [Tsai et al., Cancer Research 67(8): 3845-52 (2007); Maia et al., Molecular and Cellular Biochemistry 314(1-2): 113-121 (2008)].

To date, the majority of tumor vaccines have been evaluated in patients with the most advanced forms of disease. In the present disclosure, it was observed that the development of specific T-cell immunity in terms of positive peptide-specific tetramer and IFN-γ responses (≥4-fold increase or ≥100 pg/ml fold change, respectively) in 50% of patients vaccinated at points in the spectrum of prostate cancer that precede the development of castrate-resistance. Importantly, patients who developed augmented tetramer responses at six months compared to pre-vaccination levels had a decreased risk of biochemical progression at one year following the onset of immunotherapy. The inclusion of patients with hormone-sensitive disease who are immunologically robust, as reported herein, may be key to harnessing the full potential of novel vaccine regimens.

In summary, twenty eight HLA-A2+ patients with high-risk, locally advanced or metastatic, hormone-sensitive prostate cancer were immunized with a peptide homologue of prostate specific antigen, PSA146-154, between July 2002 to September 2004 and monitored for clinical and immune responses. Fifty percent of the patients developed strong PSA146-154-peptide specific tetramer and/or IFN-γ responses within one year and were positively correlated (p<0.001). Thirteen patients had stable or declining serum levels of PSA one year post-vaccination. A decreased risk of biochemical progression was observed in patients who developed augmented tetramer responses at six months compared to pre-vaccination levels (p=0.02). Thirteen patients have died while 15 patients remain alive with a mean overall survival of 60 months (95% CI, 51 to 68 months) per Kaplan-Meier analysis. A trend towards greater overall survival was detected in men with high-risk, hormone-sensitive CaP who developed specific T-cell immunity following vaccination with PSA146-154 peptide.

Example 2

PSA146-154 peptide vaccination by the intradermal route can be readily exported to other study sites and is amenable to multiparametric immunological monitoring that can provide accurate quantification and standardization across a trials network. The target tumor, prostate cancer, is typically indolent and, thus amenable, to immunization schema that may have long latencies to response. Prostate cancers are commonly detected and treated in low tumor burden states, an optimal condition for immunotherapeutic attempts. Relapse and progression of prostate cancer can be readily monitored and quantified by biochemical markers, well before measurable differences in standard Response Evaluation Criteria in Solid Tumors (RECIST) criteria can be observed. In sum, PSA146-154 peptide vaccine provides a promising backbone for testing and analysis of combinatorial vaccination schema envisioned by the Clinical Immunotherapy Trials Network (CITN).

Multiple immune inhibitory pathways have been implicated in prostate cancer. Programmed Death-1 (PD-1), B7 Homologue 3 (B7-H3) and B7x are especially conspicuous. Release of inhibitory signals with specific antibodies can potentiate cellular immune responses. Ipilimumab, an anti-CTLA4 mAb under development by Medarex and Bristol Myers Squibb, disrupts the interaction of Cytotoxic T-Lymphocyte Antigen 4 (CTLA-4) with B7.1 and mediates important anti-tumor effects in clinical trials. Potentiating effects also have been observed in clinical trials with the Medarex monoclonal antibody, MDX1106, which blocks the interaction of PD-1 with PD1-L. In murine models the combination of co-inhibitory blockade with the Toll-Like Receptor 9 (TLR9) agonist, CpG-Oligodeoxynucleotide (CpG-ODN) substantially augments T cell immune responses to specific peptide vaccines. An equivalent compound CPG7909 under development by Pfizer Corporation (PF351276) showed potentiating effects in clinical trials and limited toxicity at the doses used. The compound is well tolerated. We propose to move forward with phase I/II studies to evaluate whether similar synergies can be obtained in humans by vaccinating prostate cancer patients with PSA146-154 peptide in combination with a TLR9 agonists and co-inhibitory blockade of both the CTLA-4 and PD-1 pathways. Vialized PSA146-154 peptide is held under IND BB8691. A suggested protocol is outlined below:

Purpose

To test the safety and efficacy of combinatorial PSA146-154 peptide vaccination with a TLR-9 agonist and concurrent blockade of the CTLA-4 and PD-1 co-inhibitory pathways.

Specific Aims

1). To determine the safety of the combination of PSA146-154 peptide/GM-CSF vaccination with adjuvant CpG7909 plus anti-CTLA-4 mAB (ipilimumab) and anti-PD1 mAb (MDX1106) in patients with recurrent, low burden castration-resistant prostate cancer (cRPC) after primary ablative therapy.

2) To determine the efficacy of the combinatorial vaccine to elicit and sustain PSA146-154 peptide specific T cell immunity by immunomonitoring of specific Delayed Type Hypersensitivity (DTH), PSA peptide-tetramer analysis, and multiplex cytokine release assays over time.

3) To determine the correlation between the quantity and function of PSA146-154 peptide specific T cell immunity induced by vaccination at defined intervals with disease course and survival.

Endpoints
Phase I: Safety
Phase II:
1). Multiparametric quantitation of peptide specific immunity;
2). Progression Free Survival (PFS) (biochemical); Overall Survival; Quality of Life Index
3). Correlative analysis comparing actual survival outcomes to prospectively modeled survival based on Halabi normograms
Eligibility
Men of the HLA-A2.1 phenotype with asymptomatic castrate resistant PCa and projected survival of >6 mo
Inclusion
Male
Age 18 and above
Histologically proven PSA+ prostate cancer, status post primary ablative therapy of the prostate
Castrate resistant with biochemical disease recurrence, asymptomatic with no detectable metastases
Eastern Cooperative Oncology Group (ECOG) Performance Status (PS) 0-1
Life expectancy >6 months
HLA-A2.1 phenotype
Exclusion
Prior immunotherapy
Other malignancies except adequately treated basal cell or squamous cell skin carcinoma
Autoimmune disorders
Human Immunodeficiency Virus (HIV), hepatitis B, hepatitis C or other active infections
Corticosteroids or other immunosuppressive therapies
Known immunodeficiency disorders
Pprostate Specific Antigen (PSA) doubling time <2 month
Specified co-morbid conditions or organ dysfunction
White Blood Count (WBC)<2000/microliter
Absolute Neutrophil Count (ANC)<1000/microliter
Platelets<100×103/microliter
Aspartate Amino Transferase/Alanine Aminotransferse (AST/ALT)>2.5×ULN
Bilirubin >2× Upper Limit of Normal (ULN)
Serum Creat >2.0×ULN
Schema
Phase I (Cohorts of 6-12, Total of 24 Patients)
Cohort I.
PSA peptide 100 μg+GM-CSF 500 U+CpG-ODN 500 μg i.d. (PGC vaccine) weeks 1, 4 and 10 then every 6 months up to 4 years (PGC vaccine =PSA peptide+GM-CSF+CpG-ODN vaccine)
Cohort II.
PGC vaccination i.d. weeks 1, 4, and 10 then every 6 months plus:
Anti-CLTA-4 mAb (Ipilimumab) 10 mg/kg week 1, 4 and 10 then every 8 weeks to week
Cohort III.
PGC vaccination i.d. week 1, 4, and 10 then every 6 months plus:
Anti-PD-1 mAb (MDX 1106) 10/mg week 1, 4 and 10 then every 8 weeks to week 52
Cohort IV.
PGC vaccination plus anti-CTLA-4 mAb plus anti PD-1 mAb
Phase II (100 Patients, 50 Per Arm)
Arm 1. PGC vaccination (per Phase 1-Cohort 1 schedule)
Arm 2. PGC vaccination plus anti-CTLA-4 mAb and anti-PD-1 mAb
Outcomes
Immunomonitoring (baseline, week 4, 12 and 26 then annually)
Peptide specific DTH testing (biopsy of positive DTH for immunophenotyping and Chromium Release Assay (CRA)):
PSA peptide-tetramer analysis of CD8+ Peripheral Blood Lymphocyte (PBL):
Multiplex cytokine array analysis of CD8+ PBL
Gene array analysis of pre and post vaccination PBMC
Clinical monitoring (baseline, monthly×6 then every 3 months
Clinical assessment and exam
Screen for autoimmune toxicity
Complete Blood Count (CBC) and metabolic panel, Antinuclear Antibody (ANA), Coombs, Thyroid Stimulating Hormone (TSH), c-Reactive Protein (CRP)
Serum PSA (baseline, monthly×6 then every 3 months)
Bone Metabolites
Radiographic Studies as Clinically Indicated The individual components of the proposed regimen are prioritized compounds of the 2007 Immunotherapy Agent Workshop and likely to be accessible for incorporation into network studies. The proposed protocol aims to confirm preclinical studies that combined TLR stimulating adjuvants and co-inhibitory blockade can amplify peptide specific immunization to levels needed to achieve significant clinical effect. The results will be applicable to diverse tumor types for which distinguishing tumor associated peptide epitopes are identified. Favorable results will intensify the search for epitopes that will be applied to the treatment of other tumor types in the context of diverse HLA phenotypes.

Example 3

The expression of PSA is highly restricted to normal and transformed prostatic epithelial tissues. Immunohistochemical staining of prostate cancer revealed PSA-specific staining in 99% of primary and metastatic lesions [Ford et al., Br J Urol 57: 50-5 (1985)]. Thus PSA is a suitable tumor-associated antigen (TAA) for the induction of specific cytototic T lymphocytes (CTL). CTL recognize processed peptide antigens (approximately 9 to 10 amino acids in length) in association with class 1 molecules of the major histocompatibility complex (MHC), also called human leukocyte antigen or HLA [Townsend et al., Annu Rev Immunol 7: 601-24 (1989)].

Previous work by the inventors identified an HLA-A201 restricted epitope of PSA (PSA146-154 of amino acid sequence KLQCVDLHV (SEQ ID NO: 3)) that induced specific CTL responses in healthy individuals and patients with prostate cancer [Xue et al., Prostate 30(2): 73-8 (1997); Perambakam et al., Cancer Immunol Immunother 51(5): 263-70 (2002)]. Previous work by the inventors also yielded results of a clinical trial involving PSA146-154 peptide (SEQ ID NO: 3) [Perambakam et al., Cancer Immunol Immunother 55(9): 1033-42 (2006)]. Intradermal administration of peptide (SEQ ID NO: 3) admixed with GM-CSF or intravenous injection of autologous dendritic cell-bound peptide, induced specific T-cell immunity in 50% of patients with prostate cancer of HLA-A2 phenotype. Importantly, patients who demonstrated specific immunity in terms of induction of specific tetramer responses within one year of the first vaccination, showed a lower risk of serum PSA progression, further validating the efficacy of PSA146-154 peptide vaccine [Perambakam et al., Clin Dev Immunol 2010: 473453 (2010)].

Herein, the induction of specific CTL with cytolytic and cytokine activity by in vitro sensitization is reported using two long-chain synthetic peptides corresponding to human PSA protein residues, 154-173 and 210-230 in healthy individuals. In silico analysis revealed that PSA 154-173 and PSA 210-230 peptides contain multiple putative HLA binding motifs. These results open up new avenues for the PSA-based multi-peptide therapy of diverse array of prostate cancer patients.

Methods

PSA Peptides

Two long chain synthetic peptides corresponding to PSA residues 154-173 (amino acid sequence VISNDVCAQVH-PQKVTKFML; SEQ ID NO: 1) and 210-230 (amino acid sequence CALPERPSLYTKVVHYRKWIK; SEQ ID NO: 2) were purchased from Research Genetics Inc (Huntsville, Ala.) at greater than 95% purity. Peptides were dissolved in dimethyl sulphoxide at a concentration of 5 mg/ml in 2-5 ml aliquots and stored at −80° C. for long term storage.

Establishment of Specific CTL by Sensitization In Vitro

Healthy individuals were recruited in the study following informed consent of the Institutional Review Board of University of Illinois at Chicago. They were typed for HLA-ABDR per manufacturer's instructions (One Lambda Inc, CA) and peripheral blood mononuclear cells (PBMC) were obtained by ficoll-gradient centrifugation as previously described [Xue et al., Prostate 30(2): 73-8 (1997)].

CTL-PSA154-173 and CTL-PSA210-230 were induced from PBMC by multiple cycles of in vitro sensitization with respective PSA peptides as previously detailed [Xue et al., Prostate 30(2): 73-8 (1997)]. Briefly, PBMC ($1.25 \times 10^6$ per well) were stimulated with peptide (20 microgram/well) and cultured in RPMI-1640 medium containing 10% human AB serum (complete media) and rIL-2 (20 U/ml) in 24-well plates and cultured at 37° C. in 5% $CO_2$ atmosphere for 7±1 days (1 cycle). In subsequent cycles, T-cell cultures were re-stimulated with autologous irradiated PBMC ($1 \times 10^5$/well) pulsed with respective PSA peptide (SEQ ID NO: 1 or SEQ ID NO: 2). Following 5-8 cycles of stimulation, CTL were pooled and assayed for specificity and functionality as described below.

Enzyme Linked Immune-Spot Assay

The specificity of the induced CTL-PSA154-173 and CTL-PSA210-230 were evaluated in IFN-gamma enzyme linked immune-spot (ELISPOT) assay as previously detailed [Perambakam et al., Cancer Immunol Immunother 51(5): 263-70 (2002)]. Briefly, target cells (PWM stimulated autologous lymphoblasts at 10,000 cells/well) were pulsed with PSA-peptide or control HIV-RT 476-484 peptide (at 20 µg/ml) or in the absence of peptide and were co-cultured with CTL (5000 cells/well) in complete medium containing 30 U/ml of rIL-2 in 96-well polystyrene plate (Greiner, Germany) followed by incubation at 37° C. in 5% $CO_2$ atmosphere for 24 hours. The number of spot-forming cells was visualized by a two-step, purified mouse anti-human IFN-gamma capture and biotinylated mouse anti-human detection monoclonal antibody system (BD Biosciences, San Diego, Calif.). Assays were developed with an avidin-biotin complex substrate conjugate system (Santa Cruz Biotechnology, Santa Cruz, Calif.) followed by tetramethylbenzidine (TMB) liquid color developer (Sigma, St Louis, Mo.). The blue spots were counted microscopically, and the results were represented as the number of spot forming cells.

Chromium Release Assay

The cytolytic activity of induced CTL was analyzed by standard 4-hour chromium release assay as previously described [Xue et al., Prostate 30(2): 73-8 (1997)]. Briefly, targets (T2 cells) were labeled with 100 micro Curies of $Na^{51}CrO_3$ (Amersham Pharmacia Biotech, Piscataway, N.J.). Chromium labeled targets ($1 \times 10^4$/well) were then pulsed with PSA-peptide or HIV-RT 476-484 peptide or no peptide and incubated with graded number of CTL for 4 hours in 96-well 'V' bottom plate (Nunc, Naperville, Ill.). Supernatants were harvested and assayed for gamma emission using Top-count NXT scintillation counter (PerkinElmer, Waltham, Mass.) and percent lysis was calculated as detailed previously [Xue et al., Prostate 30(2): 73-8 (1997)].

Peptide-Binding Assay

The antigen-processing defective cell line, T2, was used to assay peptide binding to HLA-A201 as previously detailed [Xue et al., Prostate 30(2): 73-8 (1997)]. Briefly, T2 cells ($5 \times 10^5$/well) were pulsed with PSA-peptide or DMSO at the designated concentration and cultured in 24-well plates overnight (18 hours) at 37° C. in 5% $CO_2$ atmosphere. HLA-A2 expression was measured by flow cytometry using FITC conjugated anti HLA-A2 antibody (clone BB7.2) from BD Biosciences (San Diego, Calif.).

In Silico Analysis for HLA Peptide Binding Motifs

The 261 amino acid protein sequence (accession number P07288) obtained from national center for biotechnology was utilized as "in-put" sequence for human PSA. Bioinformatics and molecular analysis section (BIMAS) algorithm of the National Institute of Health, Bethesda, Maryland was utilized to evaluate the HLA peptide binding predictions.

Results

Induction of Specific CTL by In Vitro Sensitization of PBMC with PSA Peptides

Figure 6:
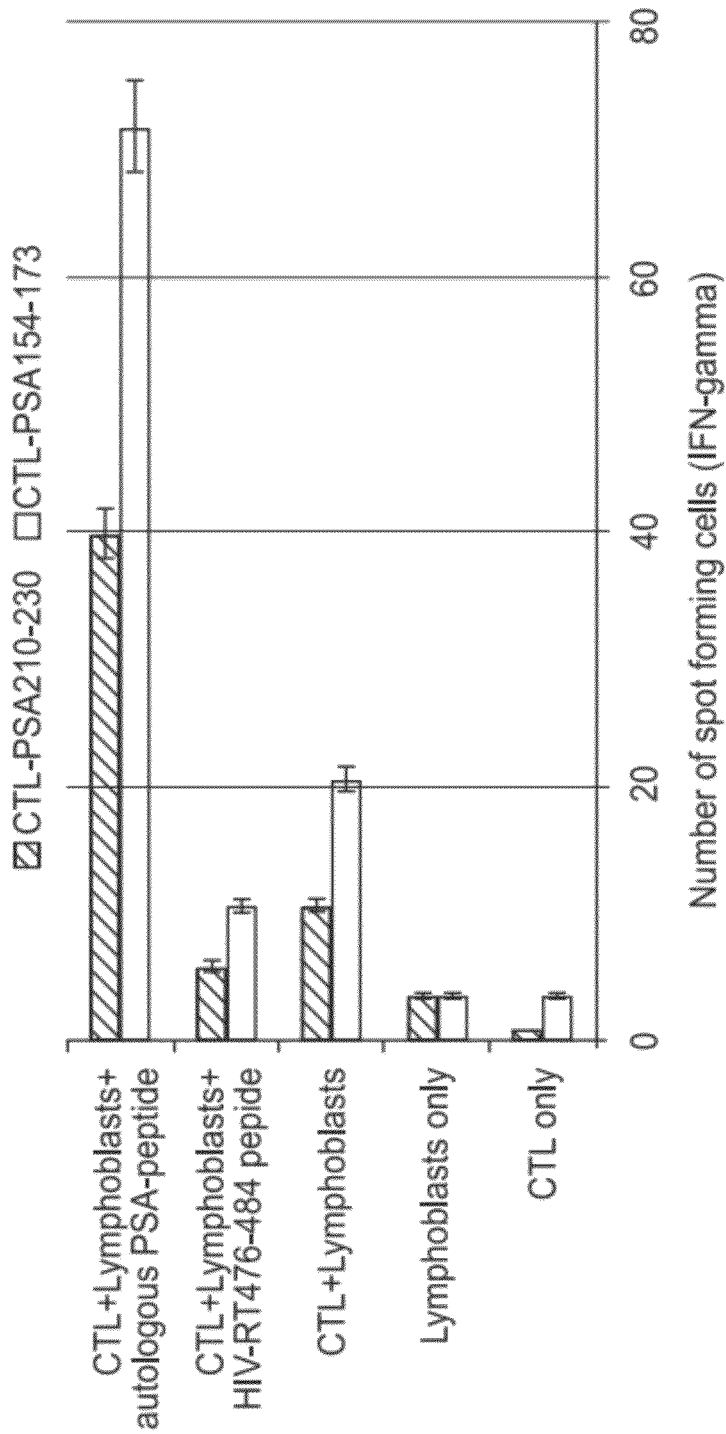
FIG. 6 shows that CTL-PSA210-230 and CTL-PSA154-173 demonstrated specific release of IFN-gamma cytokine per ELISPOT analysis.

CTL-PSA154-173 and CTL-PSA210-230 were induced by multiple cycles of in vitro sensitization of PBMC. Healthy individual was HLA-A2/A2, HLA-B61/B51 and HLA-DR4/DR10 phenotype as evaluated by HLA-ABDR typing per manufacturer's instructions (One Lambda Inc, CA). These CTL lines contained greater than 90% CD8+ T-cells as determined by flow cytometric analysis. Importantly, CTL-PSA154-173 and CTL-PSA210-230 specifically released IFN-gamma cytokine as evaluated by ELISPOT assay (FIG. 6). A greater than 3.5 fold-increase in IFN-gamma cytokine was observed against PSA-peptide pulsed autologous lymphoblasts compared to baseline levels (lymphoblasts pulsed with control HIV-RT 476-484 peptide or no peptide) for both CTLs.

Figure 7:
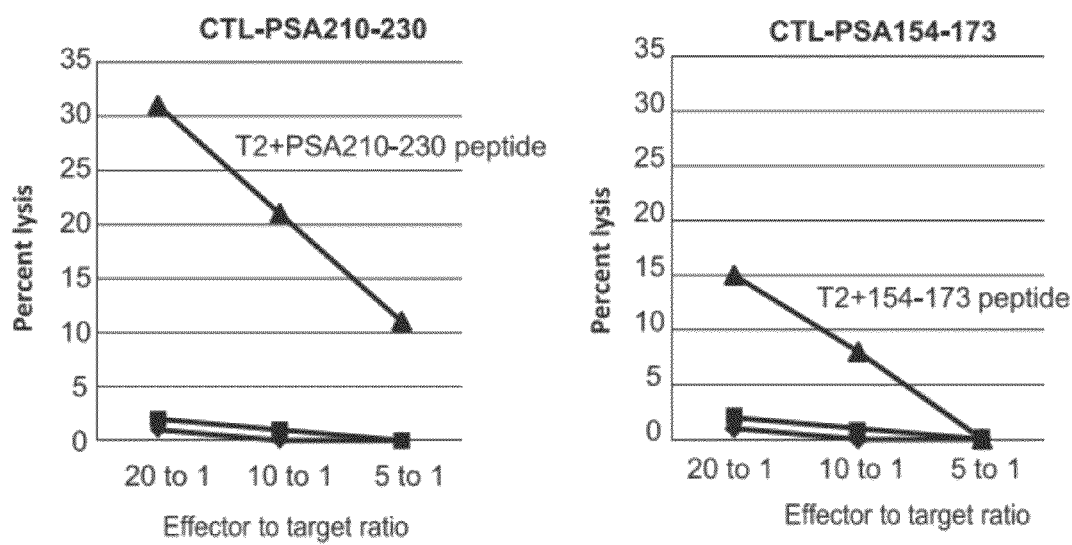
FIG. 7 shows that CTL-PSA210-230 demonstrated strong lysis of HLA-A201+ T2 targets per $^{51}$Cr release assay.

The cytolytic potential of induced CTL-PSA154-173 and CTL-PSA210-230 were evaluated in chromium release assay and results indicated specific killing of PSA-peptide pulsed T2 cells (FIG. 7). Additionally, CTL-PSA210-230 was significantly more cytolytic compared to CTL-PSA154-173 (FIG. 7). These results validated PSA154-173 and PSA210-230 peptides as potential candidates for inducing specific CTL.

Long-Chain Peptides of PSA Contain Multiple Putative HLA Binding Motifs

The ability of a peptide to elicit CTL restricted by a particular class I MHC molecule is contingent on the ability of the peptide to bind to class I MHC molecule. Therefore, the bioinformatics and molecular analysis section (BIMAS) algorithm was utilized to identify HLA peptide binding motifs. BIMAS analysis revealed that the 20-mer PSA 154-173 peptide (SEQ ID NO: 1) contained putative binding motifs for HLA-B7 and B51 (Table 6). The 21-mer PSA 210-230 peptide (SEQ ID NO: 2) included putative binding motifs for HLA-A201, A3, A1101, B7, B31 and HLA-B61 (Table 6).

Figure 8:
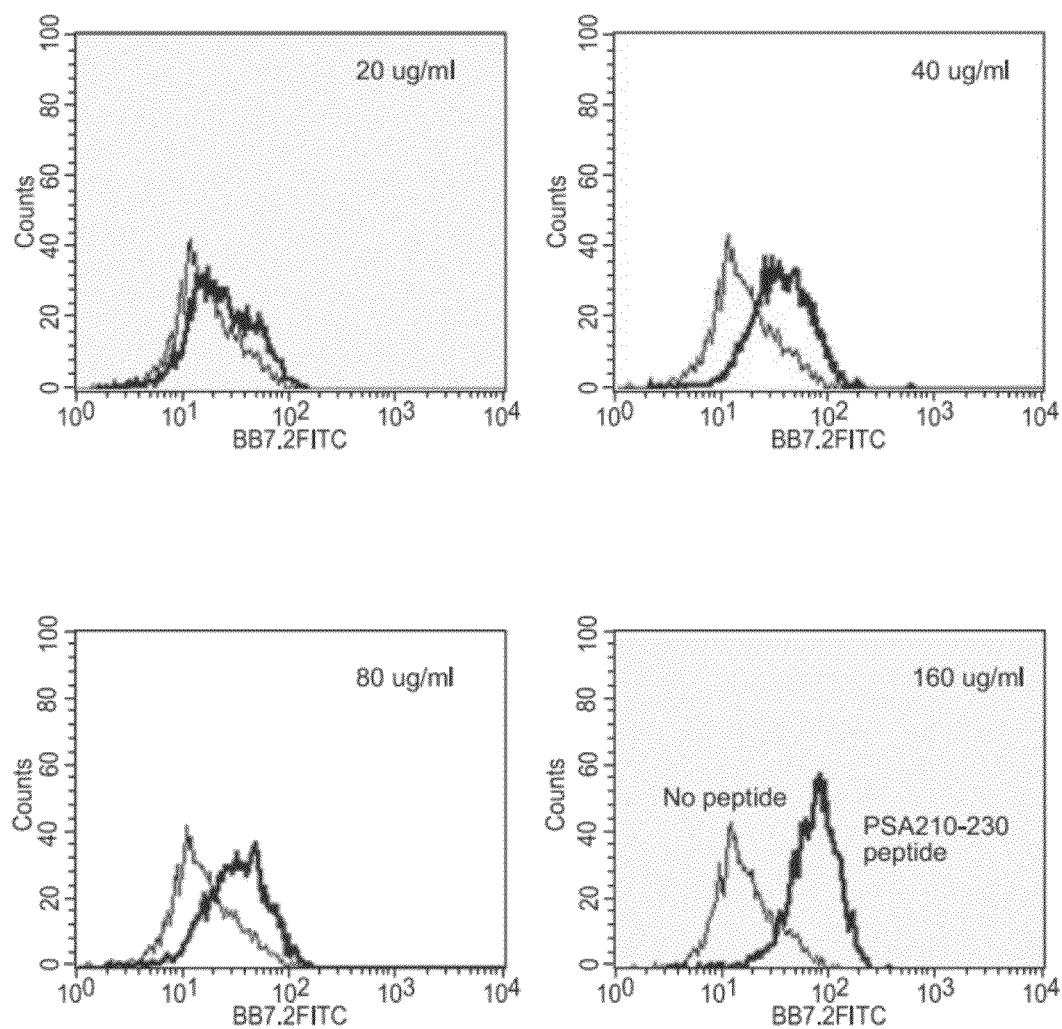
FIG. 8 shows that PSA210-230 peptide binds HLA-A0201 with high affinity in a concentration dependent fashion.

T2 binding assay was conducted to confirm the HLA-A201 binding capacity of PSA210-230 peptide and as observed, PSA210-230 peptide (SEQ ID NO: 2) binds with high affinity in a concentration dependent fashion (FIG. 8).

Example 4

Identifying Candidate Peptide Epitopes of TEM8

In silico T-cell epitope identification relies on predicting peptide binding to MHC molecules, which is the most discriminatory step in antigen presentation [Flower, Trends Immunol. 2003 December; 24(12):667-748]. Two well known computer-based algorithms, BioInformatics and Molecular Analysis Section (BIMAS) of the National Institute of Health [Parker K C, Bednarek M A, Coligan J E. Scheme for ranking potential HLA-A2 binding peptides based on independent binding of individual peptide sidechains. J. Immunol. 1994 Jan. 1; 152(1):163-75.] and "SYFPEITHI" [Rammensee et al., mmunogenetics. 1999 November; 50(3-4):213-9] were utilized to predict the binding of TEM8 peptide homologues to HLA-A0201.

Identified candidate peptides were synthesized (Protein Laboratory, Research Resources Facility, University of Illinois, Chicago) at greater than 95% purity, dissolved in dimethylsulphoxide (DMSO) at a concentration of 5 mg/ml and stored at −20° C. Peptides were tested for their ability to stabilize the expression of HLA-A2 on antigen-processing defective T2 cell line (ATCC, Manassas, Va.) as previously described [Xue et al., Prostate 1997; 30:73-78]. Briefly, 5×10$^5$ T2 cells in RPMI 1640 medium containing 10% fetal bovine serum (BioWhitaker, Walkersville, Md.) were incubated with varying amounts (1 to 80 ug/ml) of TEM8 peptide or control HIV-RT476-484 peptide, and cultured in 24 well plates for 18 hours at 37° C. HLA-A2 expression was visualized by direct staining with FITC conjugated MA2.1 antibody or an isotype control (BD Biosciences, San Diego, Calif.) followed by analysis on a FC500 flow cytometer (Beckman Coulter, Miami, Fla.).

Accordingly, six 9-mer peptides were selected based on strong predictive scores in silico (Table 7).

TABLE 6

PSA 154-173 (SEQ ID NO: 1) and PSA 210-230 (SEQ ID NO: 2) peptides contain multiple putative 9- and 10-mer HLA binding motifs*.

| Peptide position | Peptide subsequence | SEQ ID NO | HLA binding motif | Size (mer) | Ranking | Score** |
|---|---|---|---|---|---|---|
| 20-mer PSA 154-173 peptide | (VISNDVCAQVHPQKVTKFML) | | | (SEQ ID NO: 1) | | |
| 164-172 | HPQKVTKFM | 4 | B7 | 9 | 4 | 20.000 |
| 164-173 | HPQKVTKFML | 5 | B7 | 10 | 1 | 80.000 |
| 164-173 | HPQKVTKFML | 6 | B51 | 10 | 3 | 133.100 |
| 21-mer PSA 210-230 peptide | (CALPERPSLYTKVVHYRKWIK) | | | (SEQ ID NO: 2) | | |
| 211-220 | ALPERPSLYT | 7 | A0201 | 10 | 2 | 168.043 |
| 211-219 | ALPERPSLY | 8 | A3 | 9 | 5 | 6.000 |
| 222-230 | VVHYRKWIK | 9 | A3 | 9 | 6 | 6.000 |
| 221-230 | KVVHYRKWIK | 10 | A3 | 10 | 2 | 27.000 |
| 222-230 | VVHYRKWIK | 11 | A1101 | 9 | 1 | 4.000 |
| 221-230 | KVVHYRKWIK | 12 | A1101 | 10 | 1 | 18.000 |
| 222-230 | VVHYRKWIK | 13 | A3101 | 9 | 4 | 1.000 |
| 221-230 | KVVHYRKWIK | 14 | A3101 | 10 | 2 | 6.000 |
| 213-222 | PERPSLYTKV | 15 | B61 | 10 | 6 | 4.000 |

*HLA peptide binding predictions were evaluated using BIMAS algorithm.
**An estimate of half-time of disassociation of long-chain peptide or protein containing this subsequence. Only the top 6 ranking motifs (out of 20) were included.

TABLE 7

Binding ability of 9-mer HLA-A0201 peptides of Tumor Endothelial Marker-8.

| Amino acid Position | 9-mer sequence[a] | SYFPEITHI | BIMAS | T2 binding |
|---|---|---|---|---|
| 207-215 | ALQGIIHSI (SEQ ID NO: 16) | 29 | 23.995 | Yes |
| 266-274 | TLNEKPFSV (SEQ ID NO: 17) | 26 | 1653.947 | No |
| 298-306 | SMNDGLSFI (SEQ ID NO: 18) | 26 | 390.792 | Yes |
| 331-339 | FLLLALALL (SEQ ID NO: 19) | 29 | 836.253 | Not determined |
| 337-345 | ALLWWFWPL (SEQ ID NO: 20) | 24 | 1126.333 | Not determined |
| 338-346 | LLWWEWPLC (SEQ ID NO: 21) | 15 | 452.836 | Not determined |

[a]Amino acid sequence in bold phase represents dominant anchor residues while putative anchor residues are underlined.

Interestingly, the predictive binding affinities varied between the algorithms. For example, the predictive score for TEM8 207-215 was on the 'higher end' using "SYFPEITHI", while it was on the 'lower end' using BIMAS. Each of these peptides contained dominant anchor residues (depicted in bold) at the second and ninth positions according to the model proposed by Falk et al [Nature 351: 290-296, 19917]. Putative secondary anchor residues are underlined.

Figure 9:
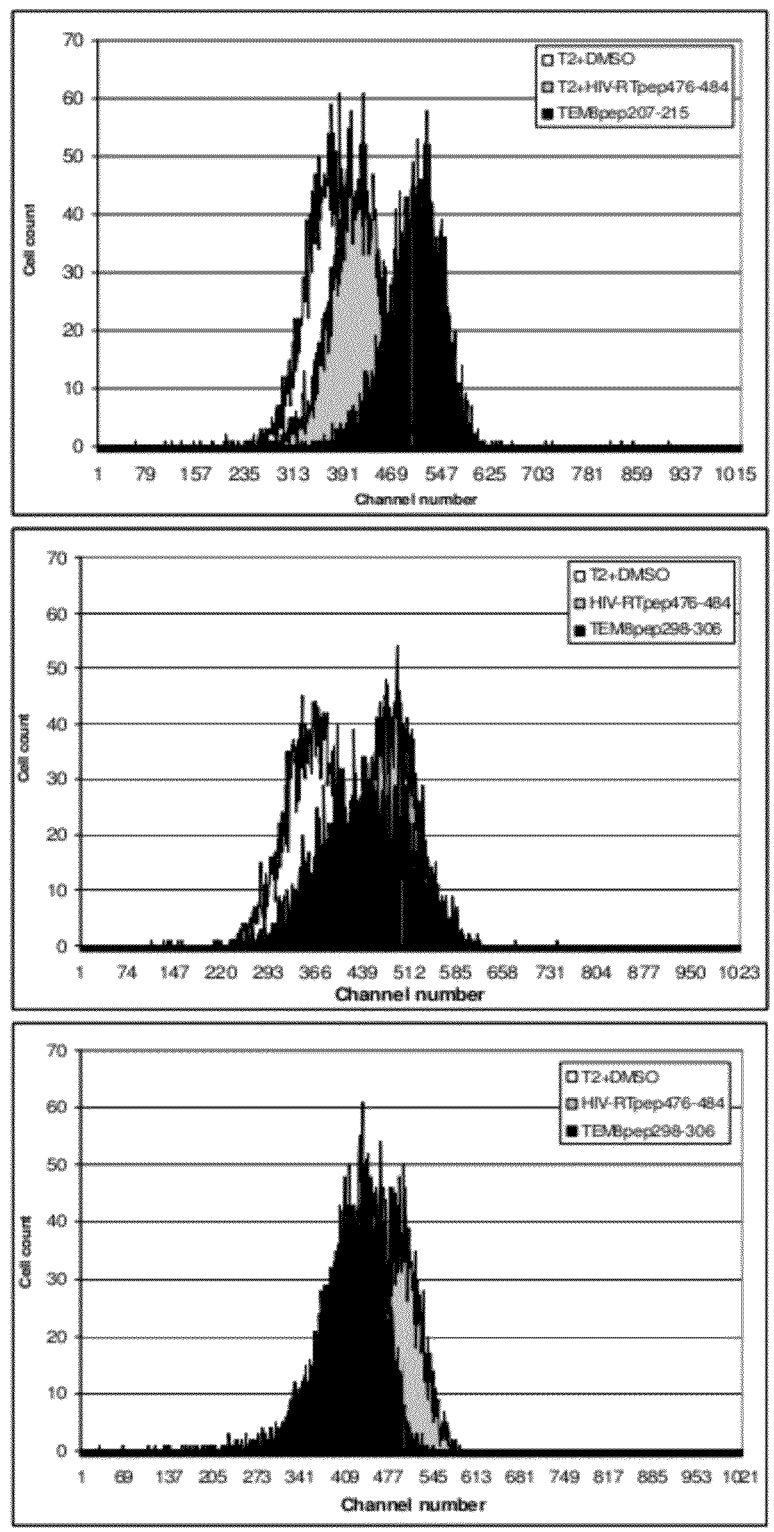
FIG. 9 shows that TEM8 peptides exhibit enhanced expression of HLA-A2. TEM8 207-215 (10 ug/ml) and TEM8 298-306 (40 ug/ml) demonstrated enhanced expression of HLA-A2 over baseline levels, i.e., T2 cells pulsed with the diluent DMSO alone, while TEM8 266-274 peptide did not. HLA-A2 expression with equivalent amounts of control HIV-RT 476-484 peptide is also shown. The results are representative of two separate experiments.

TEM8 is known to share 60% sequence homology within the extracellular integrin-like-I domain region with another protein called capillary morphogenesis protein 2 (CMG2) that is widely expressed in normal tissues [Chen et al., J Biol. Chem. 2007 Mar. 30; 282(13):9834-45. Epub 2007 Jan 24]. TEM8 337-345 and TEM8 338-346 peptides shared sequence homology with CMG2 335-343 (GLMWWFWPL; SEQ ID NO: 22) and CMG2 336-344, (LMWWFWPLC; SEQ ID NO: 23) peptides, respectively, and hence were excluded from further consideration herein. TEM8 331-339 was highly hydrophobic and was insoluble in DMSO and so it could not be tested. Three remaining peptides were tested in T2 binding assays. TEM8 207-215 and TEM8 298-306 peptides showed enhanced expression of HLA-A2 over baseline levels, while TEM8 266-274 peptide did not. TEM8 207-215 showed greater binding affinity while TEM8 298-306 peptide showed similar binding affinity in comparison to that demonstrated by HIV-RT 476-484, a known control HLA-0201 binding peptide (FIG. 9). Both these peptides were selected as potential candidate peptides of TEM8 for induction of specific HLA-A201 restricted CTL.

Example 5

TEM8 Peptide-Specific Cytolytic Activity

CTL were induced by repeated in vitro sensitization of PBMC with TEM8 207-215 and TEM8 298-306 peptides.

A healthy individual of the HLA-A2 phenotype underwent 7-9 liter leukapheresis at the Blood Donor Center following informed consent as approved by the Institutional Review Board of University of Illinois at Chicago. Peripheral blood mononuclear cells (PBMC) were obtained by separation over Ficoll-Hypaque gradient centrifugation (Amersham Biosciences, Uppsala, Sweden). PBMC were washed three times with Dulbecco's phosphate buffered saline and cryopreserved in liquid $N_2$ in a freezing mixture containing 30% plasmalyte, 10% DMSO, 10% human serum albumin (Bio-Whittaker, Walkersville, Md.).

At the time of CTL induction, PBMC were freshly thawed, washed, checked for viability and re-suspended at $1\times10^6$/ml in 10% human AB serum-RPMI 1640 medium in 24-well plates (Nunc, Naperville, Ill.). TEM8 207-215 or TEM8 298-306 peptide (50 ug/ml) and IL-7 (Pierce Endogen, Rockford, Ill.) at 10 ng/ml were added and cultured at 37° C. in a 5% $CO_2$ incubator. On day 3, IL-2 (20 U/ml) was added to the culture medium and plates were further incubated until day 7 (1 cycle). T cell cultures were re-stimulated with autologous irradiated PBMC (30 Gray) pulsed with respective peptide and re-plated in fresh medium plus cytokines weekly. The specificity of elicited CTL was tested at cycles 5 through 8.

Alternately, CTL were induced from untouched cytotoxic CD8+ T-cells using human CD8+ T cell isolation (catalogue # 130-094-156) kit (Miltenyi Biotec, Auburn, Calif.) followed by 3 cycles of in vitro sensitization with autologous irradiated peptide pulsed PBMC as described earlier.

Figure 10:
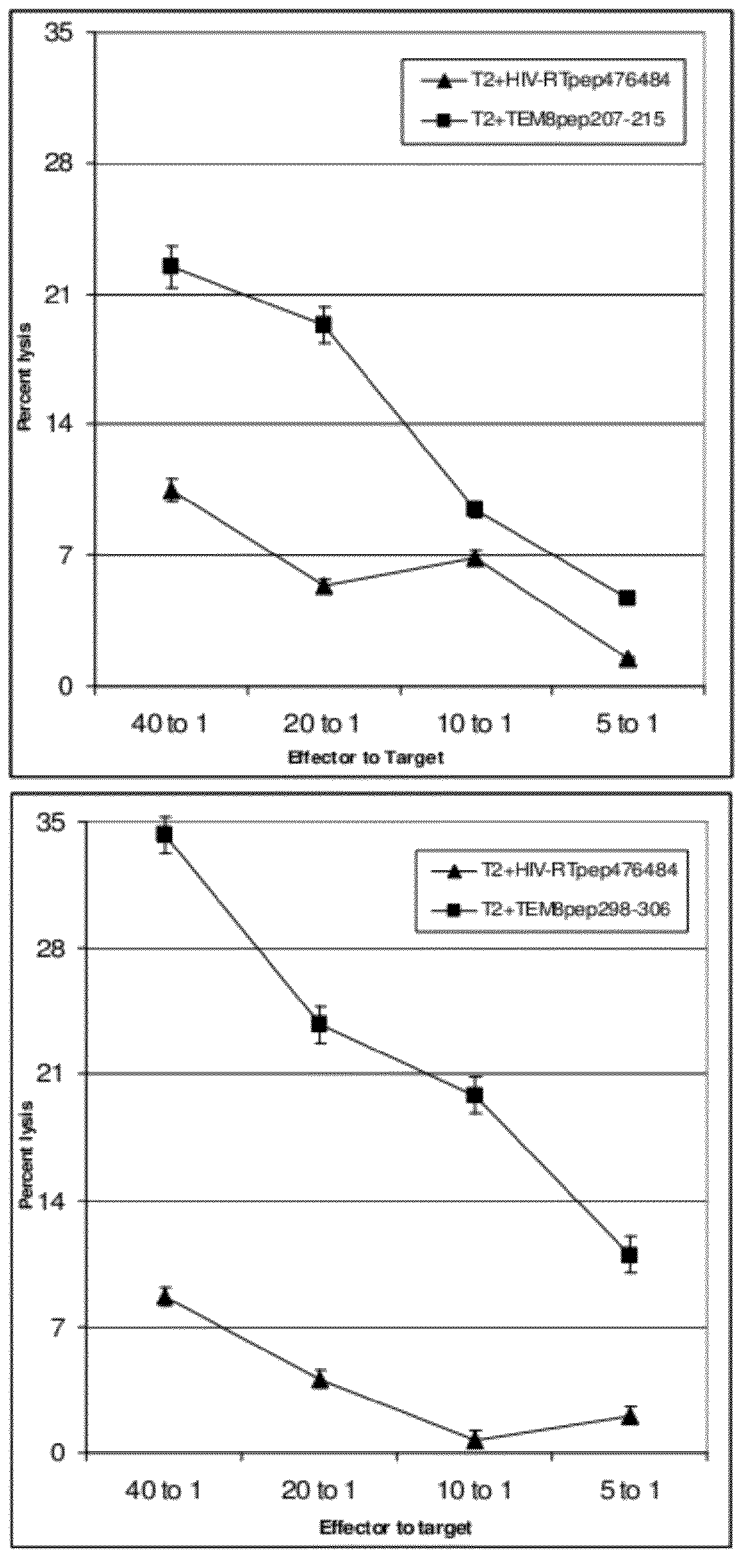
FIG. 10 shows CTL induced with TEM8 207-215 and TEM8 298-306 peptide demonstrate specific lysis of peptide-pulsed T2 cells. Cytoytic activity of CTL induced with peptides, TEM8 207-215 (upper panel) or TEM8 298-306 (lower panel) showed specific lysis of T2 cells pulsed with corresponding TEM8 (50 ug/ml) but not control HIV-RT 476-484 (50 ug/ml) peptide per chromium release assay. The results are representative of two separate experiments.

CTL induced with each of the peptides showed specific lysis of T2 cells pulsed with the respective TEM8 peptide but not control HIV-RT 476-484 peptide as assayed in 4-hour standard chromium release assay [Xue et al., Prostate 1997; 30:73-78]. Briefly, 1000 $Na^{51}CrO3$ labeled T2 cells were incubated with CTL at designated effector to target ratios in triplicates in "V" bottom 96-well plates (Nunc, Naperville, Ill.) in 10% AB-serum-RPMI 1640 medium at 37° C. in 5% $CO_2$ incubator for 4 hours. The supernatant recovered from each culture was assayed for gamma irradiation using a Top-Count NXT scintillation counter and percent specific lysis was calculated. Results are shown in FIG. 10.

CTL induced with TEM8 298-306 were strongly lytic while the CTL induced with TEM8 207-215 showed moderate cytotoxic activity.

Example 6

TEM8 Peptide-Specific Cytokine Responses

T-cells secrete distinct cytokine patterns in vitro and in vivo. In order to study the cytokine profile exhibited by TEM8 specific CTL, a multiplex cytokine array analysis was conducted.

T2 cells (25,000/well) were pulsed with TEM8 207-215 or TEM8 298-306 or HIV-RT 476-484 peptide (50 ug/ml) or treated with equivalent quantities of DMSO alone (volume by volume) then co-cultured with CTL (100,000/well) in 10% AB-serum-RPMI 1640 medium containing IL-2 (30 U/ml) in 48-well plates (Nunc, Naperville, Ill.) at 37° C. in 50% $CO_2$ atmosphere for 18 hours. Culture plates were centrifuged and supernatants were harvested and frozen at −80° C. Cytokines released into the culture supernatant were measured in triplicates with a 16-plex human cytokine Q-Plex™ array as per the manufacturer's instruction (Quansys Biosciences, Logan, Utah). Spontaneous lysis was found to be less than 10% in the experiment.

Figure 11:
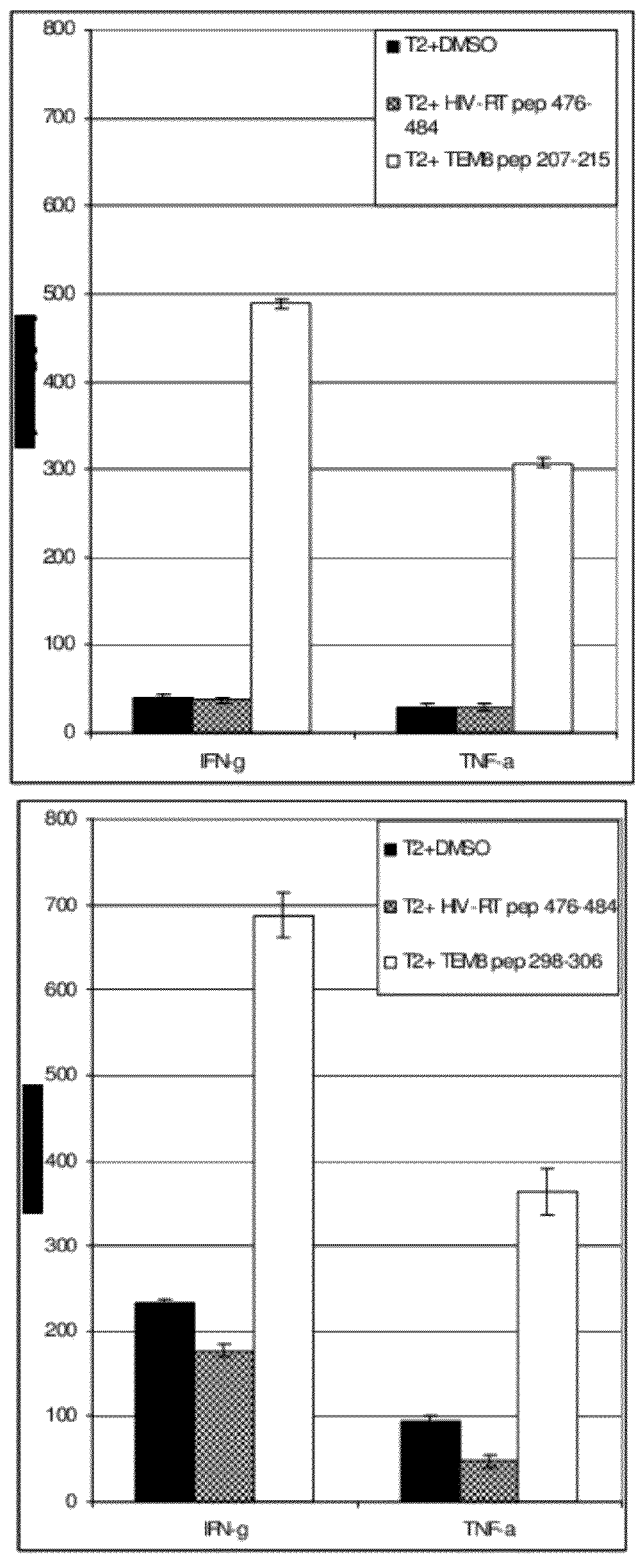
FIG. 11 shows CTL induced with TEM8 207-215 or TEM8 298-306 peptides demonstrate specific secretion of type-1 cytokines. CTL (100,000/well) induced with TEM8 207-215 (upper panel) or TEM8 298-306 peptides (lower panel) were incubated with T2 cells (25,000/well) pulsed with HIV-RT 476-484 (50 ug/ml) or TEM8 207-215 or TEM8 298-306 peptide (50 ug/ml) or equivalent amount of diluent DMSO in 10% AB serum-RPMI1640 containing IL-2 (30 U/ml) at 37° C. for 18 hours. Cytokines secreted in the medium were assayed by a 16-plex human cytokine Q-Plex™ array. Approximately a three-fold increases in interferon gamma (IFN-γ) and tumor necrosis alpha (TNF-α) was observed over baseline levels. The results are representative of two separate experiments.

CTL induced with TEM8 207-215 or TEM8 298-306 predominantly secreted type-1 cytokines, IFN-γ and TNF-α. Approximately, a three-fold increase over baseline levels was observed (FIG. 11). Secretion of type 2 cytokines IL-8 and IL-10 also was observed but at extremely low levels (Table 8).

HepG2 (HLA-A2+ TEM8+) targets with anti HLA-A2 antibody demonstrated a 2-fold inhibition of cytolytic activity. On the other hand CTL induced with TEM8 298-306 peptide demonstrated significantly lower levels of cytolytic activity against MCF-7 (HLA-A2+ TEM8-) tumor cells which was not inhibited by treatment with anti HLA-A2 antibody. This result indicates that TEM8 298-306 emulates an endogenously processed peptide epitope of TEM8 protein. A longer incubation time of 12 hours was required to observe cytolytic

TABLE 8

16-plex human cytokine Q-Plex ™ array showing specific release of cytokines in T-cell culture.

| CTL | Target | IL-1α | IL-1β | IL-2 | IL-4 | IL-5 | IL-6 | IL-8 | IL-10 | IL-12p70 | IL-13 | IL-15 | IL-17 | IL-23 | IFNγ | TFNα |
|---|---|---|---|---|---|---|---|---|---|---|---|---|---|---|---|---|
| CTLTEM8 298-306 | T2 + DMSO | <0.3 | 8.2 | 3730.2 | 2.2 | 11.6 | 4.3 | 34.9 | 74.3 | <0.3 | 739.7 | 2.2 | 0.7 | 45.2 | 233.5 | 95.3 |
| | T2 + HIV-RT476-484 | <0.3 | 2.1 | 3292.6 | 1.6 | 10.1 | 2.3 | 27.3 | 79.5 | <0.3 | 649.7 | 1 | 0.9 | 346.2 | 177 | 47.7 |
| | T2 + TEM82-306 | <0.3 | 3.5 | 2809.1 | 4.4 | 27.5 | 5.5 | 81.5 | 109.9 | 0.9 | 1022.1 | 2.1 | <0.4 | 332.3 | 687.4 | 363.4 |
| CTLTEM8 207-215 | T2 + DMSO | <0.3 | 5.1 | 2534 | 1.5 | 18.5 | 4.2 | 21.6 | 28.2 | <0.3 | 673.4 | 0.9 | 18.6 | <13.7 | 40.4 | 29 |
| | T2 + HIV-RT476-484 | <0.3 | 13.6 | 2376.9 | 1.4 | 16.5 | 3.8 | 16.8 | 22.7 | <0.3 | 389 | 1.6 | <0.4 | 18.6 | 37.2 | 29.6 |
| | T2 + TEM8207-215 | <0.3 | 5.2 | 3136.2 | 8.5 | 57.4 | 4 | 39.9 | 50.7 | 0.4 | 1599.1 | 4.9 | 2.3 | 16.1 | 488.8 | 306.7 |

*Each sample was tested in triplicate and the average value is shown (pg/ml)

CTL utilize small molecules such as perforins and granzymes to eliminate tumors. Particularly, the secretion of type-1 cytokine such as IFN-γ is crucial for tumor cell lysis [Li et al., J. Immunol. 1997 May 1; 158(9):4152-61]. Similarly, studies by Qin and co-workers have demonstrated a critical requirement of IFN-γ or IFN-γ receptor in angiogenesis associated tumor rejection involving CD8+ and CD4+ T-cells, respectively [Qin et al., Cancer Res. 2003 Jul. 15; 63(14):4095-100; Qin, Immunity. 2000 June; 12(6):677-86]. In the current study, CD4+ and CD8+ T-cells induced with TEM8 298-306 peptide demonstrated the specific secretion of type-1 cytokines IFN-γ and TNF-α, per multiplex cytokine array analysis. This finding supports the therapeutic potential of TEM8 298-306 peptide.

Example 7

Specificity of CD8+ CTL Induced with TEM8 298-306 Peptide

Cytolytic activity of CD8+ CTL was determined in a 12-hour chromium release assay. To ascertain HLA-A2 restricted activity, target cells were additionally treated with anti-HLA-A2 monoclonal antibody (BB7.2, 10 ug/ml) or equivalent amount of mouse immunoglobulin for 30 min at 37° C. prior to incubation with effector cells. Spontaneous lysis was found to be less than 12% of total lysis in the assays.

Figure 12:
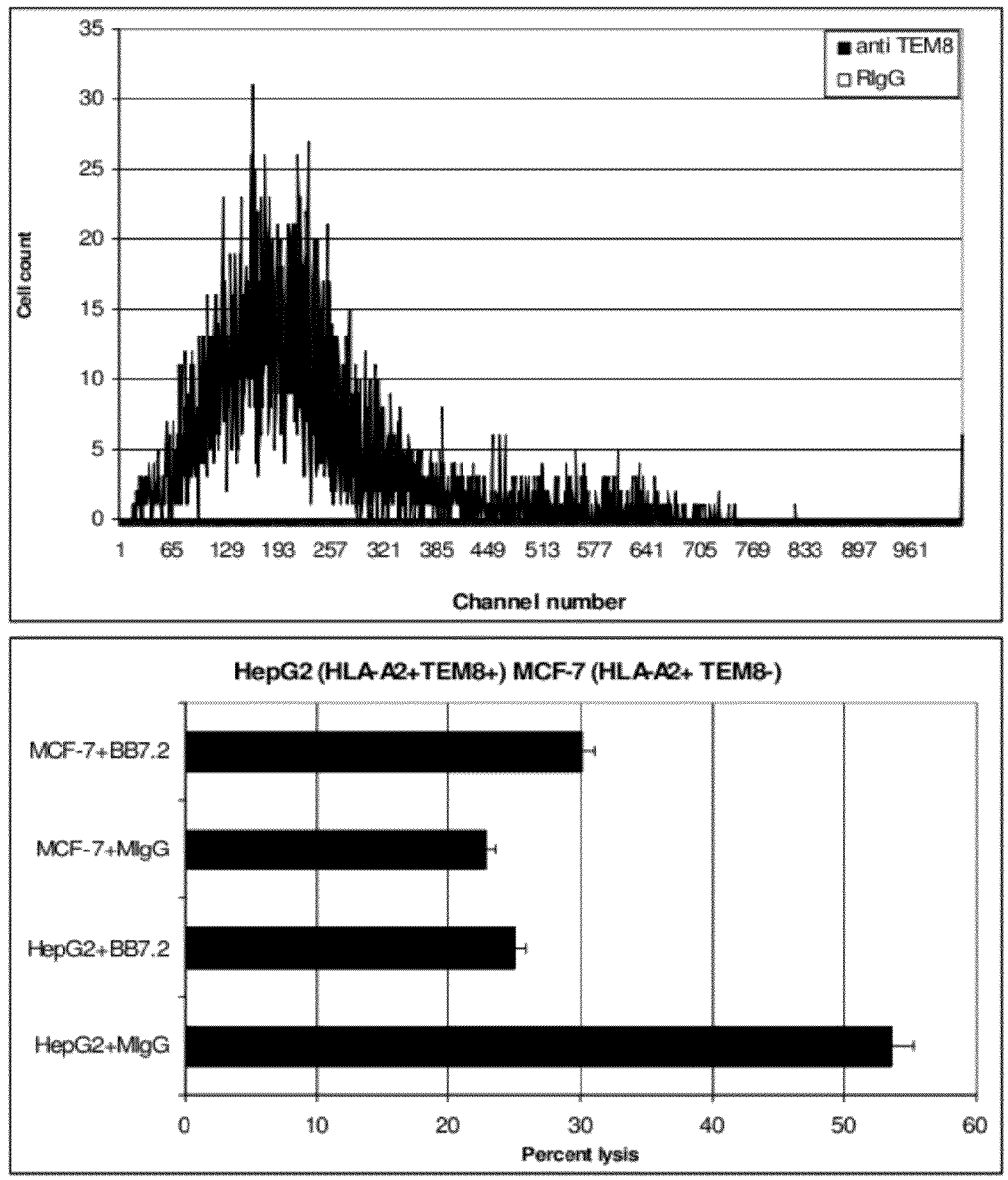
FIG. 12 shows CTL induced with TEM8 298-306 peptide demonstrate specific lysis of HepG2 tumor cell line. HepG2 tumor cells were positive for TEM8 protein (upper panel) while MCF-7 tumor cells were negative (data not shown). $^{51}$Cr labeled HepG2 (HLA-A2+ TEM8+) and MCF-7 (HLA-A2+ TEM8−) tumor cell lines (1000/well) were treated with anti-HLA-A2 monoclonal antibody (BB7.2, 10 ug/ml) or equivalent amount of mouse immunoglobulin prior to incubation with CD8+ CTL induced with TEM8 298-306 (effector to target ratio of 20 to 1). Cytolytic activity was assayed in a 12-hour chromium release assay (lower panel). The results are representative of two separate experiments.

CD8+ CTL induced with TEM8 298-306 peptide demonstrated specific recognition of TEM8+ HepG2 tumor cells line that was HLA-A2 restricted (FIG. 12). Blocking of killing of HepG2 cells. Flow cytometric analysis of HepG2 cell line using polyclonal antibody (Abcam, Cambridge, UK) revealed that 6-8% cells were positive for TEM8 protein (FIG. 12, upper panel).

Thus, CD8+ CTL induced with TEM8 298-306 peptide demonstrated specific killing of authentic tumor cells that endogenously expressed natural levels of TEM8 protein. Based on these results, TEM8 298-306 is contemplated to be useful in vaccine formulations for immunotherapy of cancers that express TEM8 in their vasculature. TEM8 peptides are administered for the targeted disruption of tumor vasculature via CTLs. Disruption of tumor vasculature in, for example, hormone, chemo- and/or radio-resistant CaP; colon cancer and breast cancer is contemplated. For CaP, patients can be treated with TEM8 and PSA peptides described herein. TEM8 is not expressed in proliferative endothelium of corpus luteum or in wound healing, therefore it is highly specific to tumor angiogenesis and not required for normal adult angiogenesis. Hence, TEM8 peptides have been selected herein as a target antigen for inducing human CTL.

While the present invention has been described in terms of specific embodiments, it is understood that variations and modifications will occur to those skilled in the art. Accordingly, only such limitations as appear in the claims should be placed on the invention.

All documents cited in this application are hereby incorporated by reference in their entirety for their disclosure described.

We claim:

1. A composition for treating cancer comprising:
   (i) a pharmaceutically acceptable carrier,
   (ii) prostate specific antigen (PSA) peptide PSA 146-154 (SEQ ID NO: 3), and
   (iii) PSA peptide PSA 154-173 (SEQ ID NO: 1), PSA peptide PSA 210-230 (SEQ ID NO: 2), tumor endothelial marker 8 (TEM8) peptide TEM8 298-306 (SEQ ID NO: 18), or combinations thereof.

2. The composition of claim 1 further comprising granulocyte macrophage colony stimulating factor (GM-CSF).

3. The composition of claim 1 further comprising a Toll-Like Receptor 9 (TLR9) agonist, an inhibitor of Cytotoxic T-Lymphocyte Antigen 4 (CTLA4), or an inhibitor of Programmed Death-1 (PD-1).

4. The composition of claim 3 wherein the TLR9 agonist is a CpG-oligodeoxynucleotide (CpG-ODN).

5. The composition of claim 3 wherein the inhibitor of CTLA4 is a monoclonal antibody.

6. The composition of claim 3 wherein the inhibitor of PD-1 is a monoclonal antibody.

7. A kit comprising a composition, instructions for administration of the composition for treating cancer, and a device for administering the composition to a patient, wherein the composition comprises:
   (i) a pharmaceutically acceptable carrier,
   (ii) prostate specific antigen (PSA) peptide PSA 146-154 (SEQ ID NO: 3), and
   (iii) PSA peptide PSA 154-173 (SEQ ID NO: 1), PSA peptide PSA 210-230 (SEQ ID NO: 2), tumor endothelial marker 8 (TEM8) peptide TEM8 298-306 (SEQ ID NO: 18), or combinations thereof.

8. The kit of claim 7 further comprising granulocyte macrophage colony stimulating factor (GM-CSF).

9. The kit of claim 7 further comprising a Toll-Like Receptor 9 (TLR9) agonist, an inhibitor of Cytotoxic T-Lymphocyte Antigen 4 (CTLA4), or an inhibitor of Programmed Death-1 (PD-1).

10. The kit of claim 9 wherein the TLR9 agonist is a CpG-oligodeoxynucleotide (CpG-ODN).

11. The kit of claim 9 wherein the inhibitor of CTLA4 is a monoclonal antibody.

12. The kit of claim 9 wherein the inhibitor of PD-1 is a monoclonal antibody.

13. A method of treating prostate cancer comprising administering to a patient in need thereof an effective amount of peptides comprising:
   (i) prostate specific antigen (PSA) peptide PSA 146-154 (SEQ ID NO: 3), and
   (ii) PSA peptide PSA 154-173 (SEQ ID NO: 1), PSA peptide PSA 210-230 (SEQ ID NO: 2), tumor endothelial marker 8 (TEM8) peptide TEM8 298-306 (SEQ ID NO: 18), or combinations thereof.

14. The method of claim 13 further comprising administering to the patient granulocyte macrophage colony stimulating factor (GM-CSF).

15. The method of claim 13 or claim 14 further comprising administering to the patient a Toll-Like Receptor 9 (TLR9) agonist, an inhibitor of Cytotoxic T-Lymphocyte Antigen 4 (CTLA4), or an inhibitor of Programmed Death-1 (PD-1).

16. The method of claim 15 wherein the TLR9 agonist is a CpG-oligodeoxynucleotide (CpG-ODN).

17. The method of claim 15 wherein the inhibitor of CTLA4 is a monoclonal antibody.

18. The method of claim 15 wherein the inhibitor of PD-1 is a monoclonal antibody.

* * * * *